United States Patent
Treace et al.

(10) Patent No.: US 10,245,086 B2
(45) Date of Patent: Apr. 2, 2019

(54) BONE PLATING KIT FOR FOOT AND ANKLE APPLICATIONS

(71) Applicant: Treace Medical Concepts, Inc., Ponte Vedra Beach, FL (US)

(72) Inventors: John T. Treace, Ponte Vedra Beach, FL (US); F. Barry Bays, Collierville, TN (US); Paul Dayton, Fort Dodge, IA (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 570 days.

(21) Appl. No.: 15/047,343

(22) Filed: Feb. 18, 2016

(65) Prior Publication Data
US 2016/0235454 A1    Aug. 18, 2016

Related U.S. Application Data

(60) Provisional application No. 62/117,788, filed on Feb. 18, 2015.

(51) Int. Cl.
*A61B 17/80*    (2006.01)
*A61B 17/84*    (2006.01)
(Continued)

(52) U.S. Cl.
CPC ...... *A61B 17/8061* (2013.01); *A61B 17/1728* (2013.01); *A61B 17/60* (2013.01);
(Continued)

(58) Field of Classification Search
CPC ............ A61B 17/7291; A61B 17/8061; A61B 17/865
See application file for complete search history.

(56) References Cited

U.S. PATENT DOCUMENTS

| 4,959,065 A | 9/1990 | Arnett et al. |
| 5,304,180 A | 4/1994 | Slocum |

(Continued)

FOREIGN PATENT DOCUMENTS

| AU | 2006252612 B2 | 4/2012 |
| CA | 2715491 C | 4/2014 |

(Continued)

OTHER PUBLICATIONS

Acumed, "Acu-Loc Wrist Plating System," Brochure and Surgical Technique, effective date Apr. 2012, reported publication date Sep. 23, 2013, 19 pages.

(Continued)

*Primary Examiner* — Anu Ramana
(74) *Attorney, Agent, or Firm* — Fredrikson & Byron, P.A.

(57) ABSTRACT

A bone plate kit may be provided for a foot or ankle orthopedic procedure, such as a lapidus procedure. In some examples, the bone plate kit includes a sterile container that holds multiple unicortical bone plate fasteners and one or more bone plates. For example, the kit may contain two bone plates configured to be used together during a tarsal-metatarsal fusion procedure. Each of the two bone plates may be configured to span different regions of a tarsal-metatarsal joint. The unicortical bone plate fasteners can be used to secure the two bone plates to the first metatarsal and medial cuneiform of a patient undergoing a procedure. In some configurations, one of the bone plates is a helical bone plate while the other bone plate may or may not be a helical bone plate.

33 Claims, 22 Drawing Sheets

(51) Int. Cl.
  *A61B 17/17* (2006.01)
  *A61B 17/60* (2006.01)
  *A61B 17/88* (2006.01)
  *A61B 17/15* (2006.01)
  *A61B 17/16* (2006.01)
  *A61B 17/64* (2006.01)

(52) U.S. Cl.
  CPC ............ *A61B 17/80* (2013.01); *A61B 17/808* (2013.01); *A61B 17/8028* (2013.01); *A61B 17/8052* (2013.01); *A61B 17/8057* (2013.01); *A61B 17/8085* (2013.01); *A61B 17/848* (2013.01); *A61B 17/8863* (2013.01); *A61B 17/15* (2013.01); *A61B 17/151* (2013.01); *A61B 17/152* (2013.01); *A61B 17/16* (2013.01); *A61B 17/6458* (2013.01); *A61B 17/8875* (2013.01)

(56) References Cited

U.S. PATENT DOCUMENTS

| | | | |
|---|---|---|---|
| 5,690,639 A * | 11/1997 | Lederer | A61B 17/8875 606/104 |
| 5,709,686 A | 1/1998 | Talos et al. | |
| 5,709,687 A * | 1/1998 | Pennig | A61B 17/80 411/368 |
| 5,785,712 A | 7/1998 | Runciman et al. | |
| 6,540,746 B1 | 4/2003 | Buehler et al. | |
| 6,786,909 B1 | 9/2004 | Dransfeld et al. | |
| 7,175,667 B2 | 2/2007 | Saunders et al. | |
| 7,344,538 B2 | 3/2008 | Myerson et al. | |
| 7,537,596 B2 | 5/2009 | Jensen | |
| 7,695,473 B2 | 4/2010 | Ralph et al. | |
| 7,785,355 B2 | 8/2010 | Mohr et al. | |
| 7,931,680 B2 | 4/2011 | Myerson et al. | |
| 8,133,283 B2 | 3/2012 | Wilson | |
| 8,162,996 B2 | 4/2012 | Schelling | |
| 8,167,918 B2 | 5/2012 | Strnad et al. | |
| 8,172,884 B2 | 5/2012 | Bouman | |
| 8,172,886 B2 | 5/2012 | Castaneda et al. | |
| 8,177,819 B2 | 5/2012 | Huebner et al. | |
| 8,177,822 B2 | 5/2012 | Medoff | |
| 8,231,662 B2 * | 7/2012 | Huebner | A61B 17/8033 606/280 |
| 8,235,994 B2 | 8/2012 | Hollawell | |
| 8,236,034 B2 | 8/2012 | Binder et al. | |
| 8,241,338 B2 | 8/2012 | Castaneda et al. | |
| 8,246,661 B2 | 8/2012 | Beutter et al. | |
| 8,257,403 B2 | 9/2012 | Den Hartog et al. | |
| 8,257,405 B2 | 9/2012 | Haidukewych et al. | |
| 8,398,687 B2 | 3/2013 | Vasta et al. | |
| 8,444,679 B2 | 5/2013 | Ralph et al. | |
| 8,512,339 B2 | 8/2013 | Medoff et al. | |
| 8,529,608 B2 | 9/2013 | Terrill et al. | |
| 8,545,540 B2 | 10/2013 | Castaneda et al. | |
| 8,652,142 B2 * | 2/2014 | Geissler | A61B 17/15 606/87 |
| 8,702,762 B2 | 4/2014 | Jacene et al. | |
| 8,734,492 B2 | 5/2014 | Mohr et al. | |
| 8,764,807 B2 | 7/2014 | Michel et al. | |
| 8,784,498 B2 | 7/2014 | Scheland | |
| 8,808,334 B2 | 8/2014 | Strnad et al. | |
| 8,828,063 B2 | 9/2014 | Blitz et al. | |
| 8,834,532 B2 | 9/2014 | Velikov et al. | |
| 8,834,537 B2 | 9/2014 | Castaneda et al. | |
| 8,852,249 B2 | 10/2014 | Ahrens et al. | |
| 8,940,029 B2 | 1/2015 | Leung et al. | |
| 9,149,313 B2 | 10/2015 | Strnad et al. | |
| 9,220,515 B2 | 12/2015 | Castaneda et al. | |
| D765,844 S | 9/2016 | DaCosta | |
| D766,434 S | 9/2016 | DaCosta | |
| D766,437 S | 9/2016 | DaCosta | |
| D766,438 S | 9/2016 | DaCosta | |
| D766,439 S | 9/2016 | DaCosta | |
| 9,452,057 B2 | 9/2016 | Dacosta et al. | |
| 2003/0060827 A1 | 3/2003 | Coughln | |
| 2004/0116930 A1 | 6/2004 | O'Driscoll | |
| 2005/0033430 A1 | 2/2005 | Powers et al. | |
| 2005/0192578 A1 | 9/2005 | Horst | |
| 2006/0116679 A1 | 6/2006 | Lutz et al. | |
| 2006/0149264 A1 | 7/2006 | Castaneda et al. | |
| 2006/0235397 A1 | 10/2006 | Sanders et al. | |
| 2006/0241607 A1 | 10/2006 | Myerson et al. | |
| 2006/0241608 A1 | 10/2006 | Myerson et al. | |
| 2006/0276795 A1 | 12/2006 | Orbay et al. | |
| 2007/0123884 A1 | 5/2007 | Abdou | |
| 2007/0191848 A1 | 8/2007 | Wack et al. | |
| 2008/0015591 A1 | 1/2008 | Castaneda et al. | |
| 2009/0118768 A1 | 5/2009 | Sixto, Jr. et al. | |
| 2009/0210010 A1 | 8/2009 | Strnad | |
| 2009/0210013 A1 | 8/2009 | Kay et al. | |
| 2009/0222047 A1 | 9/2009 | Graham | |
| 2009/0281543 A1 | 11/2009 | Orbay et al. | |
| 2010/0004691 A1 | 1/2010 | Amato et al. | |
| 2010/0023010 A1 | 1/2010 | Nelson et al. | |
| 2010/0125300 A1 | 5/2010 | Blitz et al. | |
| 2011/0008745 A1 | 1/2011 | McQuillan et al. | |
| 2011/0087295 A1 | 4/2011 | Kubiak et al. | |
| 2011/0093017 A1 | 4/2011 | Prasad et al. | |
| 2011/0137351 A1 | 6/2011 | Huebner et al. | |
| 2011/0166607 A1 | 7/2011 | Castaneda et al. | |
| 2011/0264149 A1 | 10/2011 | Pappalardo et al. | |
| 2012/0065689 A1 | 3/2012 | Prasad et al. | |
| 2012/0265204 A1 | 10/2012 | Schmierer et al. | |
| 2013/0090695 A1 | 4/2013 | Bernstein et al. | |
| 2013/0172942 A1 | 7/2013 | Lewis et al. | |
| 2013/0226248 A1 | 8/2013 | Hatch et al. | |
| 2013/0238032 A1 | 9/2013 | Schilter | |
| 2013/0261670 A1 | 10/2013 | Laeng et al. | |
| 2014/0012887 A1 | 1/2014 | Tamano | |
| 2014/0052193 A1 | 2/2014 | Prandi et al. | |
| 2014/0081341 A1 | 3/2014 | Lin et al. | |
| 2014/0107650 A1 | 4/2014 | Dacosta et al. | |
| 2014/0107798 A1 | 4/2014 | Jeng et al. | |
| 2014/0172021 A1 | 6/2014 | Castaneda et al. | |
| 2014/0180343 A1 | 6/2014 | Gaudin | |
| 2014/0214093 A1 | 7/2014 | Courtney et al. | |
| 2014/0257291 A1 | 9/2014 | Houff | |
| 2014/0277176 A1 | 9/2014 | Buchanan et al. | |
| 2015/0032168 A1 | 1/2015 | Orsak et al. | |
| 2015/0039033 A1 | 2/2015 | Biedermann | |
| 2015/0045839 A1 | 2/2015 | Dacosta et al. | |
| 2015/0313652 A1 * | 11/2015 | Burckhardt | A61B 17/80 606/71 |
| 2015/0335366 A1 | 11/2015 | Dacosta et al. | |
| 2015/0359580 A1 | 12/2015 | Dacosta et al. | |
| 2016/0030098 A1 | 2/2016 | Dacosta et al. | |
| 2016/0192970 A1 | 7/2016 | Dayton et al. | |
| 2016/0235454 A1 | 8/2016 | Treace et al. | |
| 2016/0256204 A1 | 9/2016 | Patel et al. | |

FOREIGN PATENT DOCUMENTS

| | | |
|---|---|---|
| CN | 2701408 Y | 5/2005 |
| CN | 101836888 A | 9/2010 |
| CN | 201912210 U | 8/2011 |
| CN | 102755186 A | 10/2012 |
| CN | 103892954 A | 7/2014 |
| EP | 2389884 B1 | 7/2013 |
| EP | 2441406 B1 | 9/2013 |
| ES | 2379929 T3 | 5/2012 |
| IL | 184773 A | 8/2012 |
| IN | 200607174 P1 | 8/2007 |
| KR | 101081268 B1 | 11/2011 |
| WO | 2004024009 A1 | 3/2004 |
| WO | 2006065512 A1 | 6/2006 |
| WO | 2007006430 A1 | 1/2007 |
| WO | 2007106962 A1 | 9/2007 |
| WO | 2008029142 A2 | 3/2008 |
| WO | 2008029143 A2 | 3/2008 |
| WO | 2014152535 A1 | 9/2014 |

(56) References Cited

FOREIGN PATENT DOCUMENTS

| WO | 2015094410 A1 | 6/2015 |
|---|---|---|
| WO | 2016003477 A1 | 1/2016 |
| ZA | 200808914 B | 2/2012 |

OTHER PUBLICATIONS

Acumed, "Hand Fracture System," Brochure, effective date Sep. 2014, reported publication date Jan. 29, 2016, 6 pages.
Acumed, "Hub Cap Fusion Plates," Retrieved from <http://www.acumed.net/products/hand-wrist/carpal/hub-cap-fusion-plates>, 2016, 8 pages.
Arthrex, "Plantar Lapidus Plate," 2015, 6 pages.
Arthrex, "Proximal Metatarsal Osteotomy using Plates," Retrieved from <http://www.arthrex.com/foot-ankle/proximal-metatarsal-osteotomy-using-plates>, 2016, 2 pages.
Couzens et al., "Stainless Steel Versus Titanium Volar Multi-Axial Locking Plates for Fixation of Distal Radius Fractures: A Randomised Clinical Trial," BMC Musculoskeletal Disorders, vol. 15, No. 74, Mar. 2014, 7 pages.
Diaconu et al., "Locking Plates for Fixation of Extra-Articular Fractures of the First Metacarpal Base: A Series of 15 Cases," Chirurgie de la Main, vol. 30, No. 1, pp. 26-30, Abstract only.
International Patent Application No. PCT/US2016/018495, International Search Report and Written Opinion dated Apr. 21, 2016, 10 pages.
Merete GmbH, "MetaFix OpenWedge," Retrieved from <http://www.merete-medical.com/de/produkte/fuss/hallux-valgus/metafixr-openwedge.html>, 2016, 4 pages (Google Translation).
Osteomed, "ExtremiLock Ankle Plating System," Brochure, published prior to Nov. 20, 2014, 6 pages.
Osteomed, "ExtremiLock Foot Plating System," Brochure, published prior to Nov. 20, 2014, 6 pages.
Osteomed, "Hand Plating System," Brochure, published prior to Nov. 20, 2014, 8 pages.
Plaass et al, "Anterior Double Plating for Rigid Fixation of Isolated Tibiotalar Arthrodesis," Foot and Ankle International, vol. 30, No. 7, Jul. 2009, pp. 631-639.
Plaass et al., "Placement of Plantar Plates for Lapidus Arthrodesis: Anatomical Considerations," Foot and Ankle International, vol. 37, No. 4, Apr. 2016, pp. 427-432.
Rochet et al., "Proximal Ulna Comminuted Fractures: Fixation Using a Double-Plating Technique," Revue de Chirurgie Orthopédique et Traumatologique, vol. 96, No. 7, Nov. 2010, pp. 800-807.
Smith & Nephew, Inc, "D-RAD Smart Pack," Single-Use Volar Distal Radius Plating System, Brochure, Jun. 2014, 8 pages.
Smith & Nephew, Inc, "EVOS MINI," Plating System, Brochure, May 2015, 12 pages.
Smith & Nephew, Inc, "Proximal Humerus Locking Plate," Peri-Loc Upper Extremity Locked Plating System, Surgical Technique, Sep. 2006, 36 pages.
Smith & Nephew, Inc, "Medial Column Fusion for Midfoot Deformity Correction," VLP Foot Variable Angle Locked Plating System, Surgical Technique, 2013, 20 pages.
Stryker, "Anchorage Plating System," Operative Technique, Rev. 2, Aug. 2015, 32 pages.
Stryker, "VariAx Foot Locked Plating System," Jun. 2008, 25 pages.
Synthes, "LCP Periprosthetic System," 2009, 8 pages.
Tornier, "Hand and Wrist," Retrieved from <http://www.tornier-us.com/upper/hand/>, 2016, 1 page.
Tornier, "CoverLoc Volar Plate," Retrieved from < http://www.tornier-us.com/upper/hand/writra003/>, 2016, 2 pages.
Tornier, "DFX Distal Fibula and DTX Distal Tibia Plates," Retrieved from < http://www.tornier-us.com/lower/ankle/anktra003/>, 2016, 2 pages.
Tornier, "CalcLock Extreme," Retrieved from < http://www.tornier-us.com/lower/foot/footra011/>, 2014, 2 pages.
U.S. Appl. No. 14/981,335, Bone Positioning and Preparing Guide Systems and Methods filed Dec. 28, 2015, 72 pages.
U.S. Appl. No. 62/293,189, Tarsal-Metatarsal Joint Procedure Utilizing Fulcrum filed Feb. 9, 2016, 78 pages.
Vilex, "The Vilex Plate System," Brochure, 2011, 4 pages.
Wright Medical Group N.V., "Foot & Ankle," Retrieved from < http://www.wright.com/physicians/foot-ankle>, 2016,4 pages.
Wright Medical Group N.V., "Darco Modular Rearfoot System (MRS) LPS Lapidus Plating System," Brochure, Aug. 2016, 1 page.
Zimmer, Inc. "Foot and Ankle Solutions," Retrieved from <http://www.zimmer.com/medical-professionals/products/foot-and-ankle.html>, 2014, 3 pages.
European Patent Application No. 16735405.9, Extended European Search Report dated Aug. 17, 2018, 9 pages.

\* cited by examiner

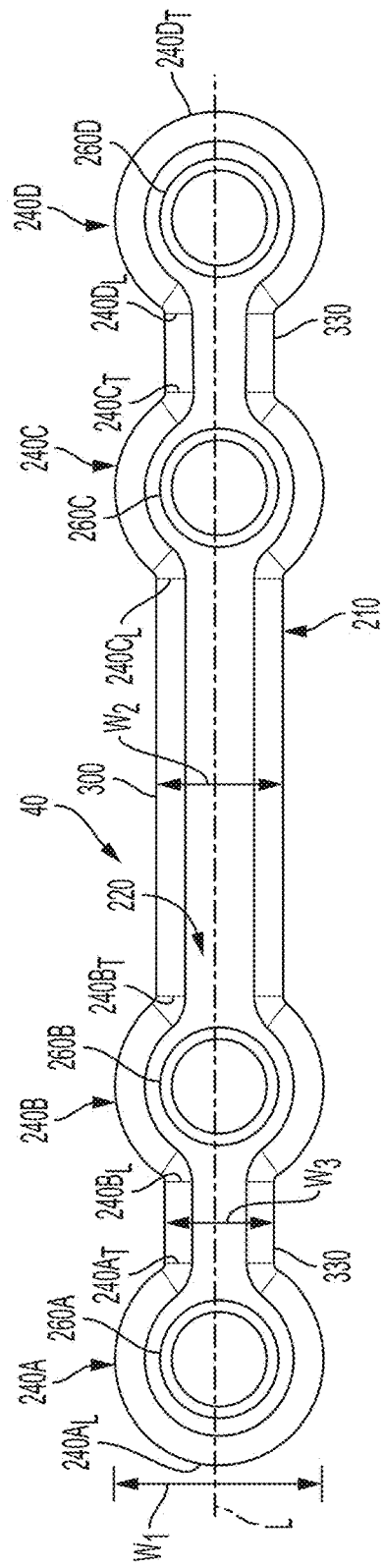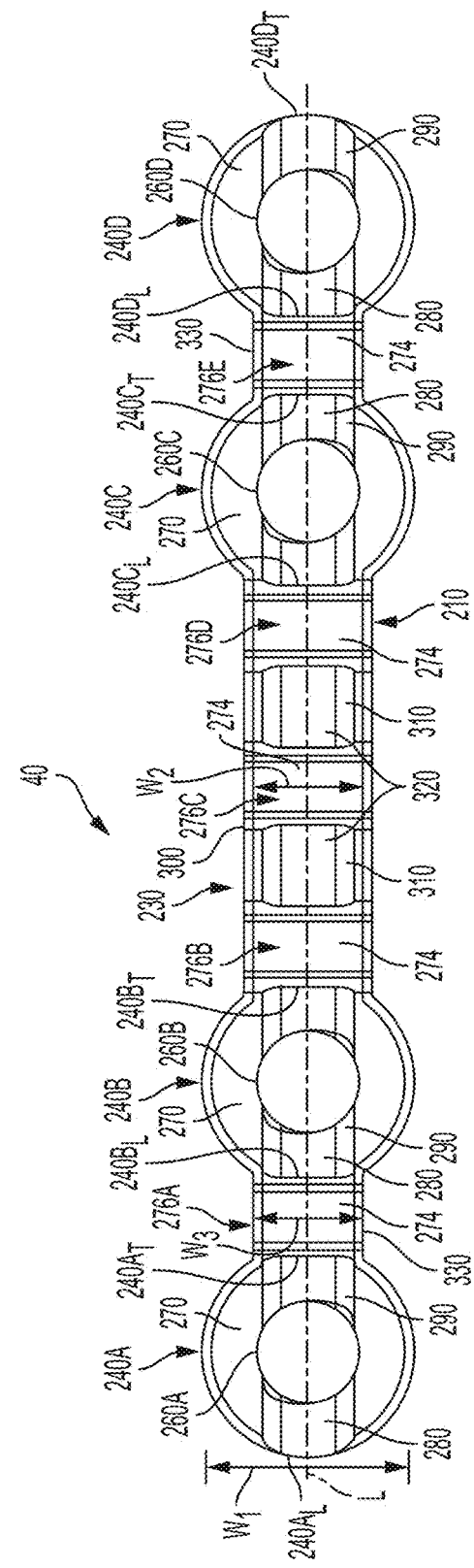

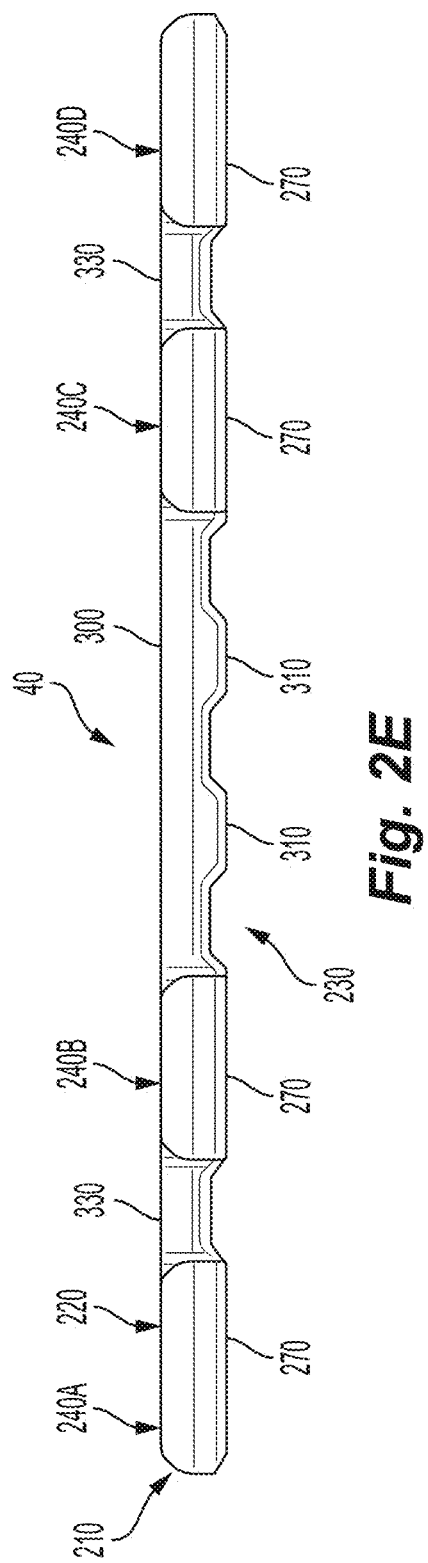
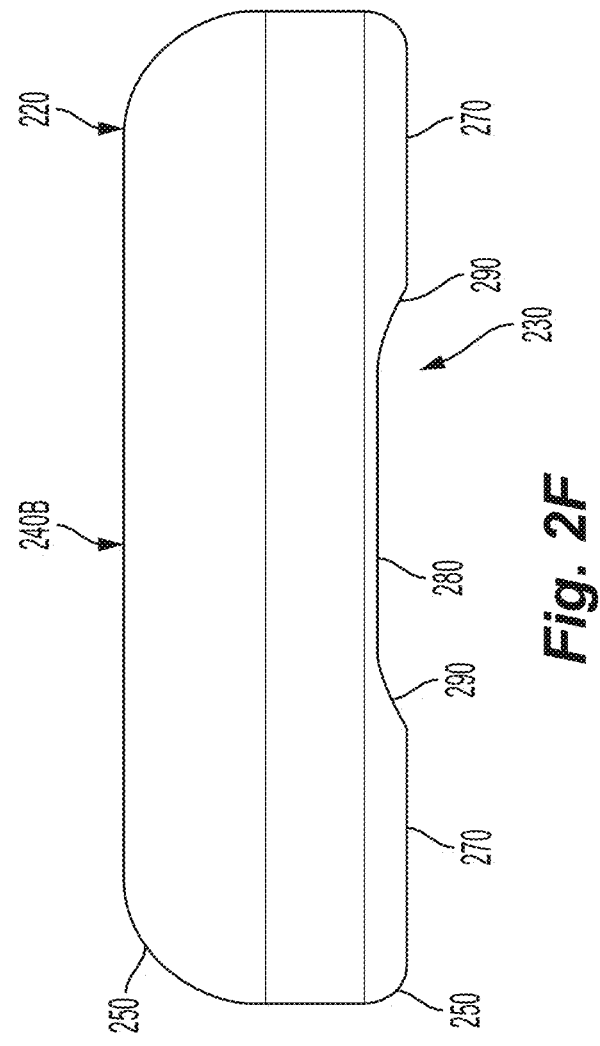
Fig. 2E
Fig. 2F

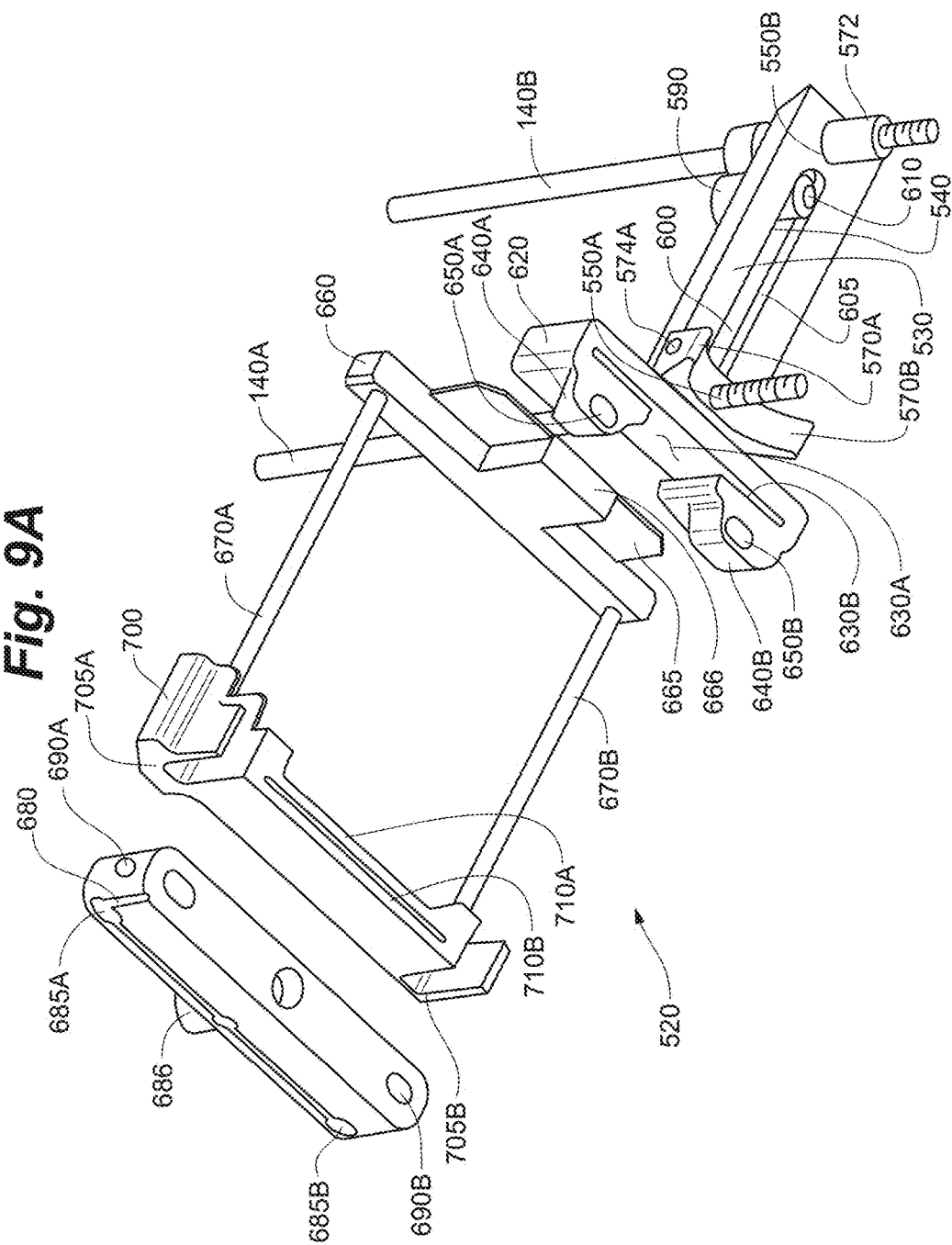

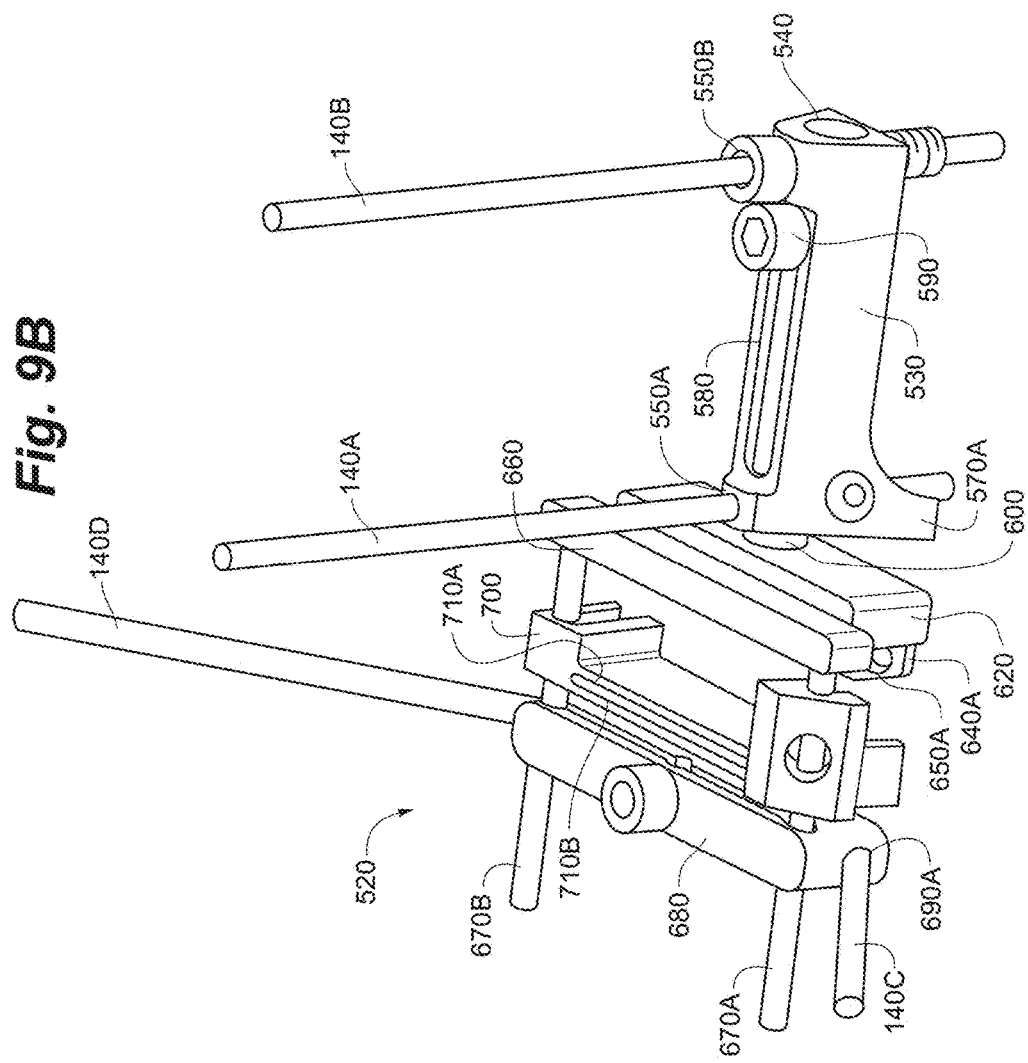

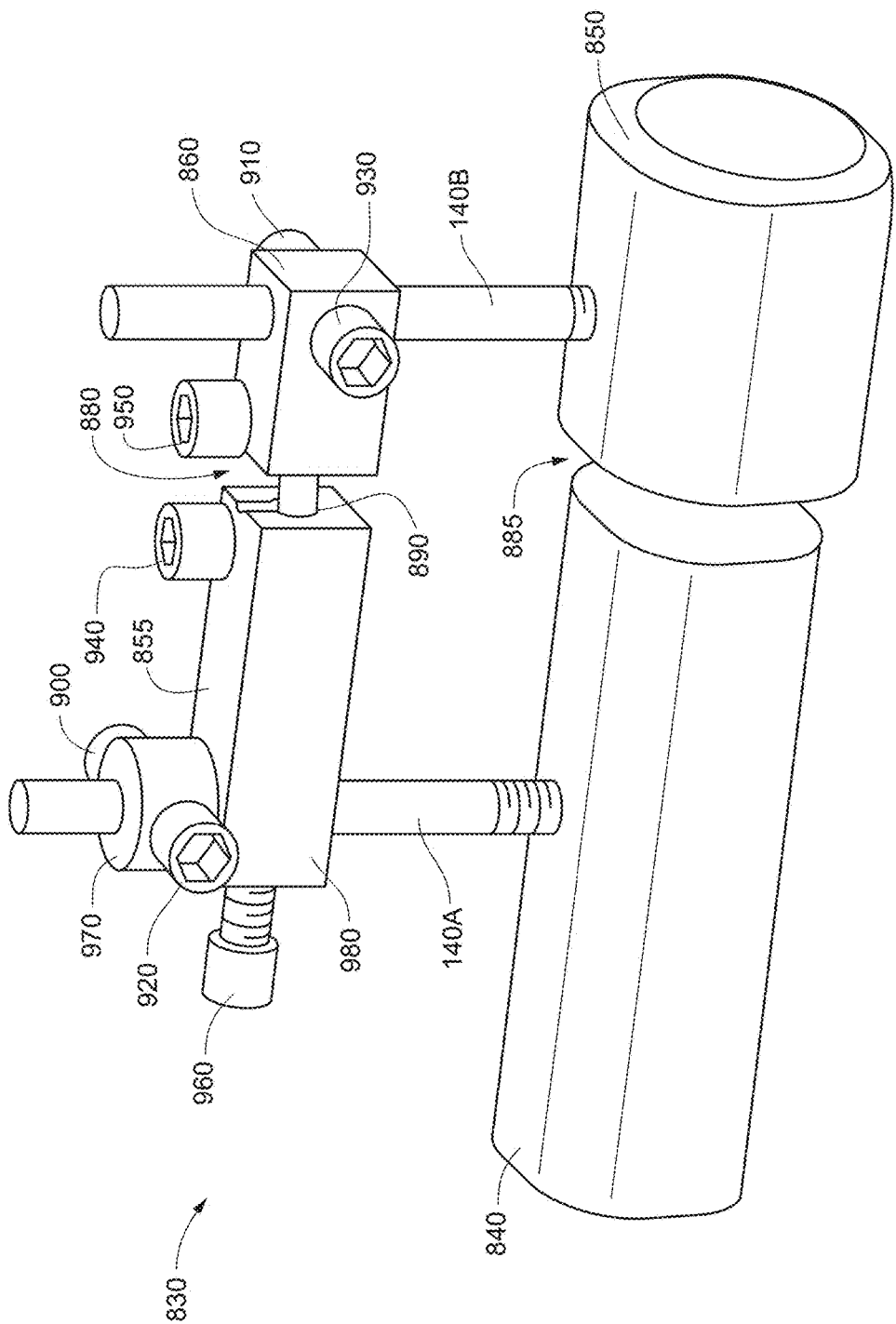

BONE PLATING KIT FOR FOOT AND ANKLE APPLICATIONS

RELATED APPLICATION

This application claims the benefit of U.S. Provisional Application Ser. No. 62/117,788, filed Feb. 18, 2015, the entire contents of which are incorporated herein by reference.

TECHNICAL FIELD

This disclosure relates to a disposable single-use surgical kit for an orthopedic procedure on a foot or ankle and methods related to the disposable single-use surgical kit.

BACKGROUND

Bones, such as the bones of a foot, may be anatomically misaligned. In certain circumstances, surgical intervention is required to correctly align the bones to reduce patient discomfort and improve patient quality of life. Surgical intervention may involve cutting one or more of the misaligned bones and then physically realigning the bones into an anatomically corrected position. A bone plate or multiple bone plates may be used to hold the bones in the anatomically corrected position, helping to prevent the bones from shifting back to their misaligned position.

SUMMARY

In general, this disclosure is directed to a bone plating kit for use in an orthopedic procedure performed on the foot and/or ankle of a patient. In some examples, the bone plating kit includes one or more bone plates and a corresponding number of bone plate fasteners that are specifically selected and configured for a particular orthopedic procedure. For example, the bone plating kit may contain two bone plates configured to be used together during a tarsal-metatarsal fusion procedure. Each bone plate may be configured (e.g., sized and/or shaped) to span different regions of the tarsal-metatarsal joint. For example, one bone plate may be configured to span from a dorsal region of a medial cuneiform to a medial region of a first metatarsal and a second bone plate may be being configured to span from a plantar region of a first metatarsal to a medial region of a medial cuneiform. To attach the two bone plates to different bones being fused, the kit may include a number of unicortical fasteners at least equal to the number of fastener openings on the bone plates within the kit. The kit may be used on a wide variety of different patients having variations in anatomy size and shape. The kit may be used in lieu of stocking a large number of different sized bone plates and fasteners.

In one example, a disposable single-use surgical kit for a foot or ankle orthopedic procedure is described that includes a sterile container, a plurality of unicortical fasteners, and at least one but no more than four bone plates, each contained within the sterile container. Each bone plate may have body having a top surface and a bone facing surface opposite the top surface as well as at least one fixation hole extending through the body from the top surface to the bone facing surface. The at least one fixation hole can be configured for receiving one of the plurality of unicortical bone plate fasteners included in the sterile container.

BRIEF DESCRIPTION OF THE DRAWINGS

FIG. 2B is a top plan view of a top surface of the bone plate of FIG. 2A.

FIGS. 2C and 2D show a top plan view and perspective view, respectively, of a bone facing surface of the bone plate of FIG. 2A.

FIG. 2E shows an elevational view of the bone plate of FIG. 2A.

FIG. 2F shows a close-up elevational end view of the bone plate of FIG. 2A.

FIG. 9A is a perspective view of a first embodiment of a bone preparation instrument with some components shown in an exploded view.

FIG. 9B is a perspective view of the bone preparation instrument of FIG. 9A assembled.

FIGS. 11A and 11B show perspective and cross-sectional views, respectively, of a third embodiment of a bone preparation instrument.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and dimensions are provided for selected elements, and all other elements employ that which is known to those of ordinary skill in the field of the invention. Those skilled in the art will recognize that many of the noted examples have a variety of suitable alternatives.

Embodiments of the present invention include a disposable single-use surgical kit. The terms "disposable" and "single-use" are meant to convey that the surgical kit, in addition to all components included in the surgical kit, is intended for use on only one surgical patient. After the surgical procedure on the one surgical patient is completed, any components that are not implanted into the one surgical patient can be discarded using conventional methods.

Examples of the disposable single-use surgical kit can be configured such that the contents of the disposable single-use surgical kit are suited for a particular surgical procedure on the one surgical patient. For instance, an exemplary disposable single-use surgical kit can include only components suited for a Lapidus/tarsal-metatarsal (TMT) fusion procedure on one surgical patient. Similarly, other exemplary disposable single-use surgical kits can include components only suited for a Metatarsal Base Wedge procedure, metatarsal-phalangeal (MTP) fusion procedure, Evans Lengthening procedure, or other procedure that addresses bone anatomy of the foot or hand of the one surgical patient.

Using a disposable single-use surgical kit configured for a specific surgical procedure on a single surgical patient may diminish the need for a surgical facility to maintain a large inventory of individual components that otherwise must be combined at the surgical facility and sterilized prior to the surgical procedure. By combining components specifically suited for the particular surgical procedure for which the kit is intended, a commonality of components can be realized which may reduce the size and complexity of the kit. Additionally, the disposable single-use surgical kit can reduce the need for assistance from agents of the component manufacturers while ensuring that the appropriate components needed for the particular procedure are available and in sterile condition. Furthermore, the disposable single-use surgical kit can be designated with a unique code in order to facilitate expensing the cost of the kit to the one surgical patient.

Figure 1:
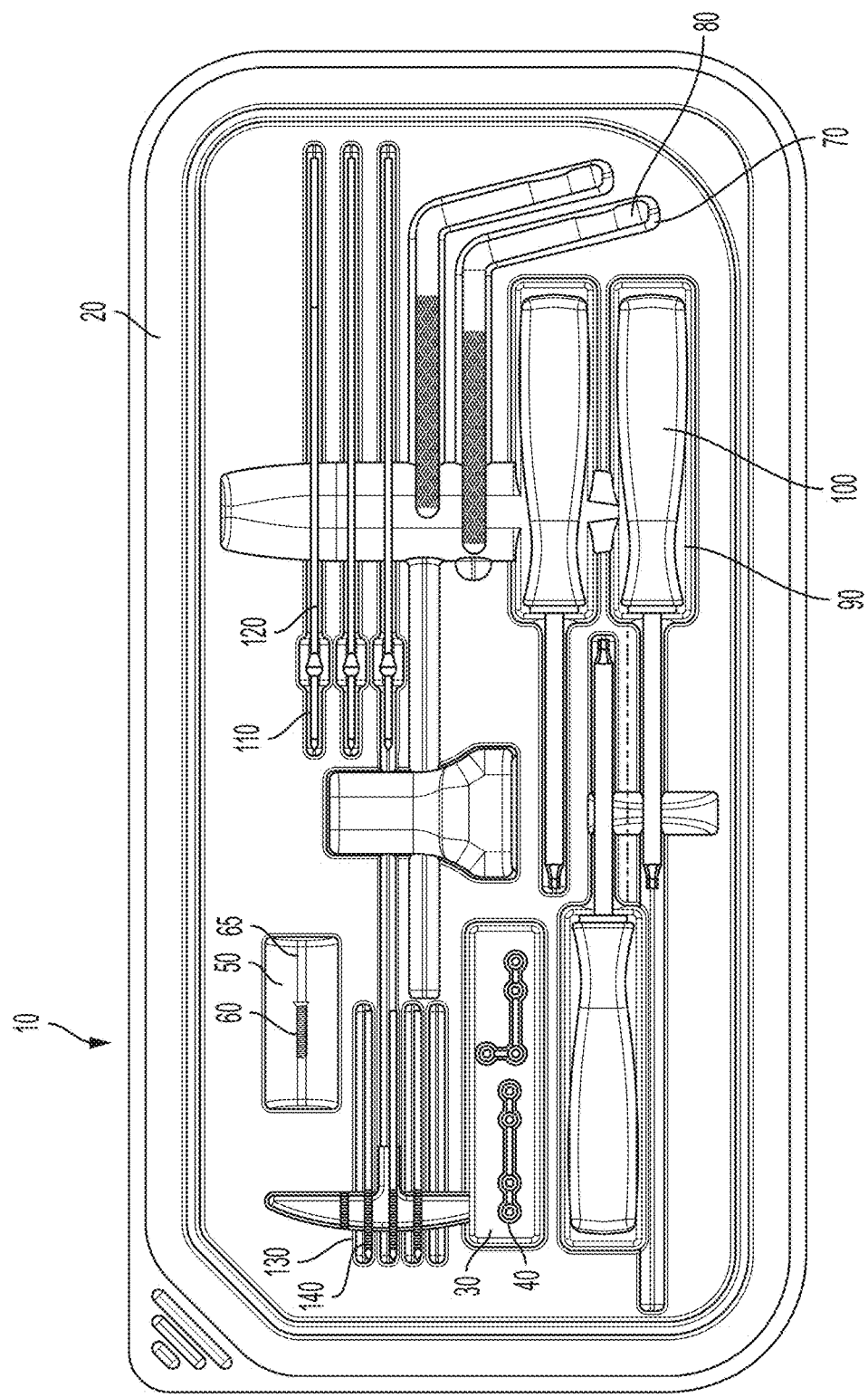
FIG. 1 is a top plan view of an embodiment of disposable single-use surgical kit including a sterile container with various surgical items in the sterile container.

FIG. 1 is a top plan view of an embodiment of a disposable single-use surgical kit 10. The kit 10 includes a sterile container 20 in which various surgical items can be contained. The container 20 can be sterilized using any appropriate sterilizing means (e.g., exposure to ethylene oxide, steam autoclave, gamma radiation). In one embodiment, the various surgical items can be placed into the container 20, and the container 20 and the various surgical items included in the container 20 can be sterilized in a single step. The sterile container 20 may be partially or wholly enclosed in a packaging that can serve to protect the container 20 as well as seal and maintain a sterility of the container 20. The packaging and/or the sterile container 20 can be made of a transparent material, such as an appropriate polymer, to allow viewing of the surgical items included in the container 20.

As noted, the disposable single-use surgical kit 10 can include various surgical items which may be retained in the sterile container 20. Embodiments of the kit 10 can include different surgical items and/or different quantities of similar surgical items depending on the specific surgical procedure for which the particular embodiment of the kit 10 is to be used on the single surgical patient.

For example, the embodiment of the kit 10 illustrated in FIG. 1 has a partition 30 for retaining one or more bone plates 40. The partition 30 may, for instance, be integrally formed in the container 20 and used to compartmentalize the one or more bone plates 40 from the remainder of the container 20. The partition 30 can be configured (e.g. sized, shaped) to retain the one or more bone plates 40 within the container 20 until the one or more bone plates 40 are removed from the container 20 at an appropriate time, such as during a surgical procedure and immediately prior to installation. In some embodiments, the container 20 can include at least one bone plate 40 but no more than four bone plates 40 (e.g. only one, two, three, or four bone plates). Including at least one and no more than four bone plates 40 in the container 20 of the kit 10 allows the kit 10 to be a disposable single-use surgical kit used for a specific surgical procedure on a single surgical patient. The at least one and no more than four bone plates 40 included in the container 20 can have similar or different configurations. Details on example configurations of the at least one and no more than four bone plates 40 will be discussed with reference to later figures.

The kit 10 can also have a partition 50 for retaining a plurality of bone plate fasteners 60 in the container 20. In some embodiments, the partition 50 can include a slot 65 configured to hold the bone plate fasteners 60 in a manner that allows the bone plate fasteners 60 to slide along a longitudinal axis of the slot 65. In some embodiments, a number of bone plate fasteners 60 included in the container 20 is equal to a total number of fixation holes (shown, e.g., in FIG. 2B) of the bone plates 40 included in the container 20. In other embodiments, the number of bone plate fasteners 60 included in the container 20 is equal to a total number of fixation holes of the bone plates 40 included in the container 20 plus one additional bone plate fastener 60. For example, where two bone plates 40 are included in the container 20 and each of the two bone plates 40 has four fixation holes (for a total of eight fixation holes), the number of bone plate fasteners 60 included in the container 20 can be nine. In yet other embodiments, the number of bone plate fasteners 60 included in the container 20 is equal to a total number of fixation holes of the bone plates 40 included in the container 20 plus two additional bone plate fasteners 60. In certain embodiments, the number of bone plate fasteners 60 included in the container 20 is equal to a total number of fixation holes of the bone plates 40 included in the container 20 plus three additional bone plate fasteners 60. In a specific embodiment, the number of bone plate fasteners 60 included in the container 20 is equal to a total number of fixation holes of the bone plates 40 included in the container 20 plus four additional bone plate fasteners 60.

Including one, two, three, or four bone plate fasteners 60 more than the number of fixation holes of the bone plates 40 included in the container 20 can be beneficial in instances where bone plate fasteners 60 may be dropped or lost during a surgical procedure. Overall, including a number of bone plate fasteners 60 in the container 20 equal to a total number of fixation holes of the bone plates 40 included in the container 20 and optionally plus one, two, three, or four additional bone plate fasteners 60 allows the kit 10 to be a disposable single-use surgical kit used for a specific surgical procedure on a single surgical patient. In certain embodiments, no bone plate fasteners 60 more than a total number of fixation holes of the bone plates 40 included in the container 20 or more than a total number of fixation holes of the bone plates 40 included in the container 20 plus one, two, three, or four are included in the kit 10.

In addition to the bone plates 40 and the bone plate fasteners 60, the kit 10 may additionally have partitions 70 for retaining plate manipulation instruments 80. In some embodiments, the container 20 can include at least one and no more than three plate manipulation instruments 80. The kit 10 can also have partitions 90 for retaining driver members 100. In some embodiments, the container 20 can include at least one and no more than three driver members 100. Furthermore, the kit 10 may have partitions 110 for retaining bone cut pins 120. In certain embodiments, the container 20 can include at least one and no more than four bone cut pins 120. Additionally, the kit 10 can have partitions 130 for retaining bone preparation fixation pins 140. The container 20 may have at least one and no more than ten bone preparation fixation pins 140. Although not shown in FIG. 1, the container 20 may also have a partition adapted to receive a bone preparation instrument and the kit 10 can include at least one bone preparation instrument. Including the specified number of surgical items in the container 20 allows the kit 10 to be a disposable single-use surgical kit used for a specific surgical procedure on a single surgical patient.

The kit 10 shown in FIG. 1 is only exemplary. Other embodiments of a disposable single-use surgical kit may not include one or more of the surgical items shown in FIG. 1 and/or may include surgical items in addition to those shown in FIG. 1. However, in some embodiments, if a particular surgical item is included in an embodiment of a disposable single-use surgical kit, the quantity of that surgical item in the kit is within the quantity ranges noted herein.

Figure 2A:
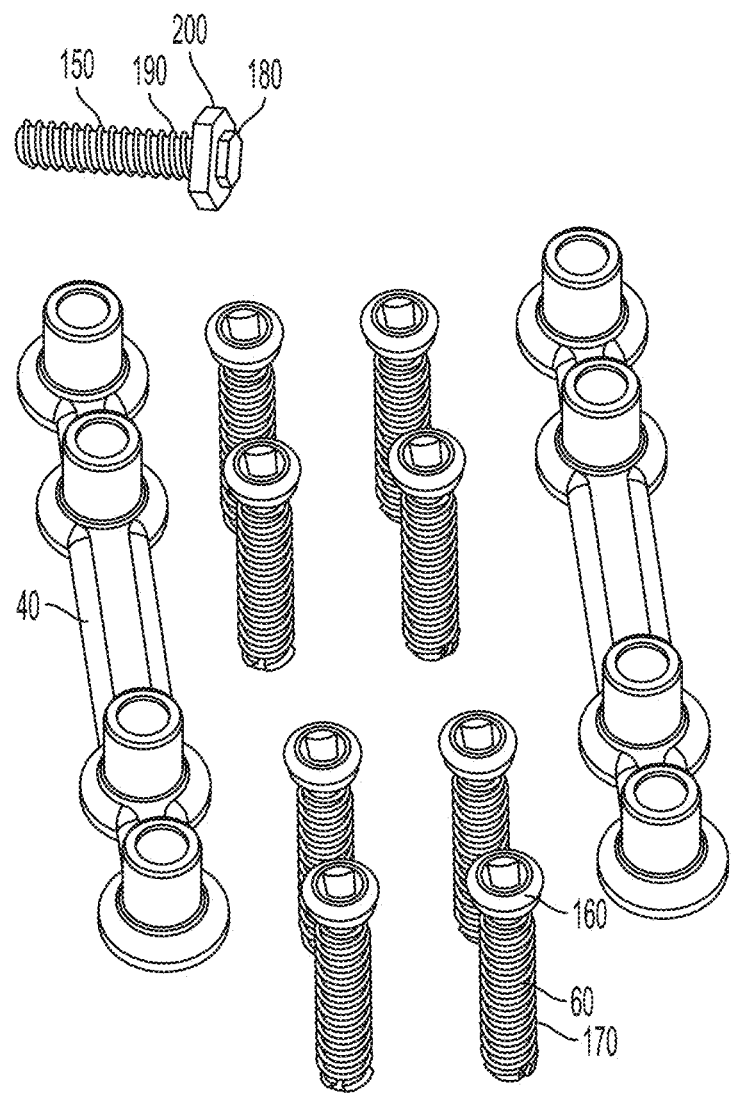
FIG. 2A is a perspective view showing embodiments of bone plates, bone plate fasteners, and an external fastener with a washer.

FIGS. 2A-2H show the bone plates 40. FIG. 2A shows a perspective view of the bone plates 40, as well as the bone plate fasteners 60 and an external fastener 150. Each of the bone plate fasteners 60 can have a head 160 attached to a shaft 170. The head 160 of each bone plate fastener 60 may be the same size (e.g. same diameter). At least a portion of the shaft 170 of each bone plate fastener 60 can include a threading, and such threading may mate with threading in fixation holes of bone plates. The shaft 170 of each of the bone plate fasteners 60 can have a length that is one of a first length, a second length, a third length, or a fourth length. The shaft 170 of each one of the bone plate fasteners can have a diameter that is one of a first diameter, a second diameter, a third diameter, or a fourth diameter. Consequently, in some embodiments, the bone plate fasteners 60 included in the kit 10 of FIG. 1 have shafts 170 with no lengths other than the first, second, third and/or fourth lengths and/or no diameters other than the first, second, third and/or fourth diameters. In other words, in some embodiments the kit 10 can include bone plate fasteners 60 with at most four different lengths and/or at most four different diameters. The bone plate fasteners 60 included in the kit 10 can have lengths that are the same or any combination of the first, second, third, and/or fourth lengths. The bone plate fasteners 60 included in the kit 10 can also have diameters that are the same or any combination of the first, second, third, and/or fourth diameters. And the bone plate fasteners 60 included in the kit 10 can have lengths and diameters that are the same or any combination of the first, second, third, and/or fourth lengths and the first, second, third, and/or fourth diameters. The bone plate fasteners 60 can be used to secure the bone plates 40 to one or more bones.

In some applications, one or more (e.g., all) of the bone plate fasteners 60 in the kit are unicortical bone plate fasteners. Cortical bone is one of the two types of osseous tissue that form bones. As its name implies, cortical bone forms the cortex, or outer shell, of a bone. Accordingly, a unicortical bone plate fastener may be configured (e.g., sized) to be inserted through one cortical surface of the bone but not an opposed cortical surface. For example, the tip of the unicortical bone plate fastener may reside within the cancellous or spongy bone of a bone structure (e.g., with the shaft extending through the first cortex and into the medullary structure of the bone structure) rather than passing through two cortical walls of the bone. The unicortical fastener may pass through a bone plate (e.g., with a head of the fastener bearing against the plate) and a tip of the fastener within the intramedullary cannel surrounded by cancellous bone, once installed and securing the bone plate to a desired bone. The use of unicortical bone plate fasteners instead of bicortical bone plate fasteners may help reduce the number of different sized and/or shaped fasteners required to be included in kit 10.

Other accessory screws not to intended or configured to be inserted through the fixation holes of the bone plates (e.g., bone plate 40) may be included in kit 10. For example, FIG. 2A illustrates external fastener 150 that may be included in the kit. Embodiments of the kit 10 can include in the container 20 at least one and no more than two external fasteners 150. The at least one and no more than two external fasteners 150 can have a head 180 attached to a shaft 190. At least a portion of the shaft 190 can include a threading. A washer 200 may be disposed around the shaft 190, and as such the washer 200 can be sized appropriately to receive the external fastener 150 via the shaft 190. Additionally, the at least one and no more than two external fasteners 150 may be sized different than the bone plate fasteners 60 included in the container 20, such that, for example, the external fasteners 150 have a diameter different (e.g., greater) than a diameter of the bone plate fasteners 60 and/or a length different (e.g., greater) than a length of the bone plate fasteners. The at least one and no more than two external fasteners 150 can be used, with or without washers 200, as a separate bone fixation means independent of the bone plates 40. For example, the external fastener 150 can have an end (e.g., an end of the external fastener 150 opposite an end near which the washer 200 is disposed) inserted into a bone such to provide additional fixation of that bone.

Figure 2D:
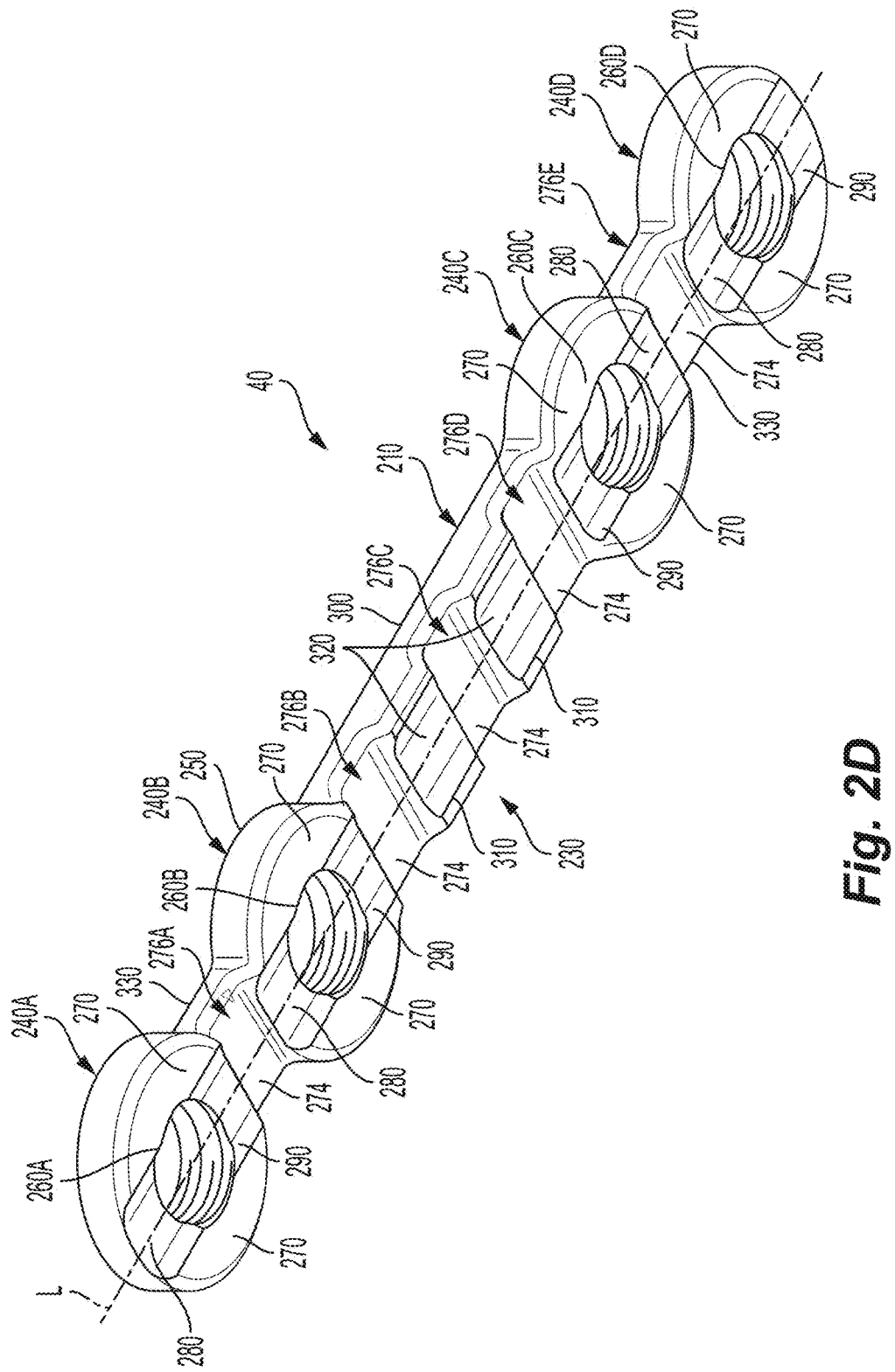

FIGS. 2B-2F illustrate an embodiment of a bone plate 40 that defines a body 210. FIG. 2B illustrates a top plan view of a top surface 220 of the body 210, while FIGS. 2C and 2D illustrate a top plan view and perspective view, respectively, of a bone facing surface 230 of the body 210. For convenience, "bone facing surface" will refer to all surfaces generally facing bone when the plate is positioned on a bone, regardless of whether those surfaces are in the same plane. FIG. 2E is a side elevational view of the bone plate 40, and FIG. 2F is a close-up end elevational view of a portion of the bone plate 40.

The body 210, as noted, can include the top surface 220 and the bone facing surface 230, which is on a side of the body 210 opposite the top surface 220. In an exemplary application, the bone plate 40 can be positioned so that the bone facing surface 230 is made to interface with a bone. Additionally, the body 210 has a length defining a central longitudinal axis L and one or more widths $W_1$, $W_2$, and $W_3$ defining an extent of the body 210 (and thus the bone plate 40) transverse to the central longitudinal axis L. Although the bone plate 40 is illustrated as lying in a single plane along the axis L, in other embodiments the bone plate 40 can include curvature or bending of the body 210 along or around the axis L such that the body 210 of the bone plate 40 does not lie in a single plane.

The body 210 may include regions 240A, 240B, 240C, and 240D extending from the top surface 220 to the bone facing surface 230, and which can be spaced from one another along the axis L. Regions 240A, 240B, 240C, and 240D can each extend a distance along the axis L from a region leading edge $240A_L$, $240B_L$, $240C_L$, and $240D_L$ to a region trailing edge $240A_T$, $240B_T$, $240C_T$, and $240D_T$, respectively. The width $W_1$ can correspond to a width of the body 210 at each region 240A, 240B, 240C, and 240D, and in the illustrated embodiment the width $W_1$ is the greatest extent of the body 210 transverse to the axis L.

As shown for example in FIG. 2F, region 240B has an outer shape 250 that links the top surface 220 and the bone facing surface 230. The outer shape 250 may be any type of contour at region 240B that reduces stress or increases strength of the bone plate 40. The outer shape 250 can also be used to minimize soft tissue irritation and increase bone healing during application of the bone plate 40. In the illustrated embodiment, the outer shape 250 includes a rounded edge contour that can increase strength for bending of the bone plate 40, reduce stresses in the bone plate 40 for improving the useful life of the bone plate 40, and reduce soft tissue irritation and increase bone healing when the bone plate 40 is utilized. Regions 240A, 240C, and 240D can also include outer shapes 250.

Included at the regions 240A, 240B, 240C, and 240D can be fixation holes 260A, 260B, 260C, and 260D, respectively. Fixation holes 260A, 260B, 260C, and 260D extend through the body 210 at regions 240A, 240B, 240C, and 240D, respectively, from the top surface 220 to the bottom surface 230. Fixation holes 260A, 260B, 260C, and/or 260D may be configured to receive fasteners, such as bone plate fasteners 60. For example, holes 260A, 260B, 260C, and/or 260D can be threaded to threadingly engage bone plate fasteners 60. As a result, the fixation holes 260A, 260B, 260C, and 260D may serve as a location for fixing the bone plate 40 to a bone.

In the illustrated embodiment the bone plate 40 has four regions 240A, 240B, 240C, and 240D and four fixation holes 260A, 260B, 260C, and 260D, but in other embodiments any number of regions and fixation holes can be included regardless of whether a particular region also includes a fixation hole. Additionally, the regions 240A, 240B, 240C, and 240D on the body 210 are shown as rounded, but in other embodiments the regions 240A, 240B, 240C, and 240D can have various other geometries. Where the regions 240A, 240B, 240C, and 240D are rounded, in one embodiment one or more of the regions 240A, 240B, 240C, and/or 240D may have a radius of curvature between about 2.7 mm and about 3.0 mm (e.g., 2.9 mm). Moreover, although the regions 240A, 240B, 240C, and 240D are illustrated to be of similar sizes, the regions 240A, 240B, 240C, and 240D can also be of varying sizes. For example, one region can include the width $W_1$ while another region may have its greatest width less than the width $W_1$, or greater than the width $W_1$.

Located on the bone facing surface 230 at a region 240A, 240B, 240C, or 240D can be a pad 270 that extends outward a distance from a first surface 274 (labeled in FIGS. 2C-D). In the embodiment shown, the first surface 274 is included on a region 276A that includes the thinnest cross-section of the bone plate 40. One or more additional regions 276B-E may be provided, each having the first surface 274 at generally the same elevation. In one application, the pad 270 can extend outward from the first surface 274 in a direction that is generally perpendicular to the first surface 274, but in other applications the pad 270 can extend out from the first surface 274 at various angles. In one example, the pad 270 extends outward about 0.3 millimeters to about 0.5 millimeters (e.g., about 0.42 millimeters) relative to the first surface 274. For instance, where the pad 270 extends out perpendicular to the surface 274 a ratio of a thickness of the bone plate 40 including the pad 270 to a thickness of the bone plate 40 at the first surface 274 can be between approximately 1.01 and 1.5 (e.g., about 1.3).

Thus, the pad 270 can be a point of contact with a bone on the bone facing surface 230 when the bone plate 40 is configured to interface with the bone. As shown, the bone facing surface 230 of the bone plate 40 includes a pad 270 at each of the regions 240A, 240B, 240C, and 240D such that the pads 270 are adjacent the fixation holes 260A, 260B, 260C, and 260D at the respective regions. In the illustrated embodiment, the pads 270 extend a length along the axis L from each region leading edge $240A_L$, $240B_L$, $240C_L$, and $240D_L$ to each region trailing edge $240A_T$, $240B_T$, $240C_T$, and $240D_T$, respectively. The pads 270 as shown also extend from a first end of the width $W_1$ of the body 210 to a first point on a perimeter of the fixation holes 260A, 260B, 260C, and 260D nearest the first end of the width $W_1$, and from a second end of the width $W_1$, located opposite the first end of the width $W_1$, of the body 210 to a second point on the perimeter of the fixation holes 260A, 260B, 260C, and 260D nearest the second end of the width $W_1$. Thus, in the embodiment shown the pads 270 do not span an entire width, including width $W_1$, of the regions 240A, 240B, 240C, and 240D on the bone facing surface 230. In some embodiments, the sum total of the surface area of the pads on a bone plate is less than 50% of the total surface area of the bone plate. Although the embodiment of bone plate 40 shown includes the pads 270 adjacent the fixation holes 260A, 260B, 260C, and 260D, any number of the pads 270 can be included at various locations on the bone facing surface 230 and the geometries of the pads 270 can vary according to the particular application of the bone plate 40.

The span of the pads 270 along the width of the regions 240A, 240B, 240C, and 240D is interrupted in the embodiment of bone plate 40 by channels 280 in the pads 270 at each of the regions 240A, 240B, 240C, and 240D. In the embodiment shown, the channels 280 extend outward a distance from the first surface 274, but in other embodiments the channels 280 can be flush with the first surface 274. In embodiments where one or more channels 280 do extend out a distance from the first surface 274, the distance these one or more channels 280 extend out is less than the distance the pads 270 extend out from the first surface 274. In such embodiments, the pads 270 are raised relative to the channels 280, and the channels 280 are elevated relative to the first surface 274, as shown in FIG. 3B. The channels 280 may extend a length along the axis L on the bone plate 40 from each region leading edge $240A_L$, $240B_L$, $240C_L$, and $240D_L$ to each fixation hole 260A, 260B, 260C, and 260D of the respective region and from each fixation hole 260A, 260B, 260C, and 260D to each respective region trailing edge $240A_T$, $240B_T$, $240C_T$, and $240D_T$. The channels 280 may also extend a width along the width of each region 240A, 240B, 240C, and 240D between the pads 270. As such, in the illustrated embodiment fixation holes 260A, 260B, 260C, and 260D interface with the pads 270 or the channels 280 at all locations along the perimeters of the fixation holes 260A, 260B, 260C, and 260D. As shown, each channel 280 included at each region 240A, 240B, 240C, and 240D is aligned along the axis L with the channels 280 at each other region.

At locations where the channel 280 interfaces with the pad 270, a radiused surface 290 can be included to transition from the channel 280 to the pad 270. For example, the radiused surface 290 can have a continual slope from the raised pad 270 to the relatively lower channel 280. The radiused surface 290 may act, for example, to reduce stresses in the bone plate 40, and therefore can be useful for applications of the bone plate 40 where a greater strength is desired.

Including one or more pads 270 and/or one or more channels 280 can provide benefits during application of the bone plate 40. For instance, including a pad 270 and/or a channel 280 on the bone facing surface 230 may decrease trauma to a periosteal membrane of a bone when the bone plate 40 is attached to a bone in a surgical procedure. Decreasing trauma to the periosteal membrane of the bone can result in less disruption of blood flow, which can help with healing the area of the bone interfacing with the bone plate 40.

Additionally, the pad 270 and/or channel 280 can act to increase a bending strength of the bone plate 40 without impeding bending of the bone plate 40 in a desired location of bone plate 40. In certain embodiments, a desired location of bone plate bending includes at least one of the regions 276A-E. In such embodiments, one or more of the regions 276A-E can be configured to concentrate bending forces applied to the bone plate 40. In a particular embodiment, such regions are configured to concentrate bending stresses by having a smaller minimum bending force required to bend the plate at the region compared to other regions of the plate. In the embodiment shown, the smaller minimum bending stress is provided by the regions 276A-E having the thinnest cross-sections of the plate. Thus, this can allow the bone plate 40 to be bent as desired for a particular application and anatomy without deforming any threads included in any of the fixation holes 260A-D.

Extending along the axis L between regions 240B and 240C, and forming part of the body 210, can be a bridge 300. The bridge 300 may define a portion of the body 210 having a width $W_2$. In the exemplary embodiment of the bone plate 40 shown, the width $W_2$ along the bridge 300 can be less than the width $W_1$ included at regions 240A, 240B, 240C, and 240D, but in other embodiments the bridge 300 can have widths $W_2$ equal to or greater than the width $W_1$. The bridge 300 as illustrated has sides running parallel to the axis L that are generally linear, but for other embodiments of the bone plate 40 the bridge 300 can have rounded sides similar to the regions 240A, 240B, 240C, and 240D or any other geometry suited for the specific application of the bone plate 40. In some embodiments, the bridge 300 is devoid of any apertures and extends between regions having fixation holes, such as regions 240B and 240C having fixation holes 260B, 260C, respectively.

On the bone facing surface 230, the bridge 300 may include one or more pads 310. The one or more pads 310 can be similar to the pad 270, such that the one or more pads 310 extend outward from the first surface 274. Also on the bone facing surface 230, the bridge 300 can have one or more channels 320 included along the width $W_2$ between the pad 310. The one or more channels 320 can be similar to the channel 280. In the embodiment shown, the channels 320 extend outward a distance from the first surface 274, but in other embodiments the channels 320 can be flush with the first surface 274. In embodiments where one or more channels 320 do extend out a distance from the first surface 274, the distance these one or more channels 320 extend out is less than the distance the pads 310 extend out from the first surface 274. In such embodiments, the pads 310 are raised relative to the channels 320, and the channels 320 are elevated relative to the first surface 274, as shown in FIG. 2D. In one exemplary application, the one or more channels 320 can be aligned with the channels 280 along the axis L. Further, the one or more channels 320 can extend outward the same distance as the channels 280 from the first surface 274. In addition, the one or more channels 320 can have the same width as the channels 280. Any of these embodiments can result in a continuous channel that is formed at all locations on the bone facing surface 230 along the axis L having a pad 270 or 310.

The bridge 300 as shown has two pads 310, the first pad 310 bordered by regions 276B and 276C, and the second pad 310 bordered by regions 276C and 276D, each pad 310 having a channel 320 located along the width $W_2$ between the pad 310, spaced along the axis L. In other embodiments of the bone plate 40 the bridge 300 can include any number and configuration of pads 310 and channels 320. The pads 310 and channels 320 may serve similar functions to those described with respect to the pads 270 and channels 280. Further, regions 276B-D can be configured as desired bending regions as described above for regions 276A and E.

Extending along the axis L between regions 240A and 240B as well as between regions 240C and 240D are branches 330. The branches 330 form a portion of the body 210 that connects the region 240A to the region 240B as well as the region 240C to the region 240D. The branches 330 have a width $W_3$. The width $W_3$ of the branches 330 as illustrated in less than the width $W_1$ and $W_2$, but in other embodiments the width $W_3$ can be equal to or greater than the width $W_1$ and/or the width $W_2$. Thus, for the bone plate 40 illustrated in FIGS. 2B-2F the width of the body 210 is greatest at the regions 240A, 240B, 240C, and 240D and least at branches 330. The branches 330 as shown have sides running parallel to the axis L that are generally linear, but for other embodiments of the bone plate 40 the branches 330 can have rounded sides similar to the regions 240A, 240B, 240C, and 240D or any other geometry suited for the specific application of the bone plate 40. In the embodiment shown, the branches include the first surface 274 and coincide with regions 276A and 276E.

Figure 2G:
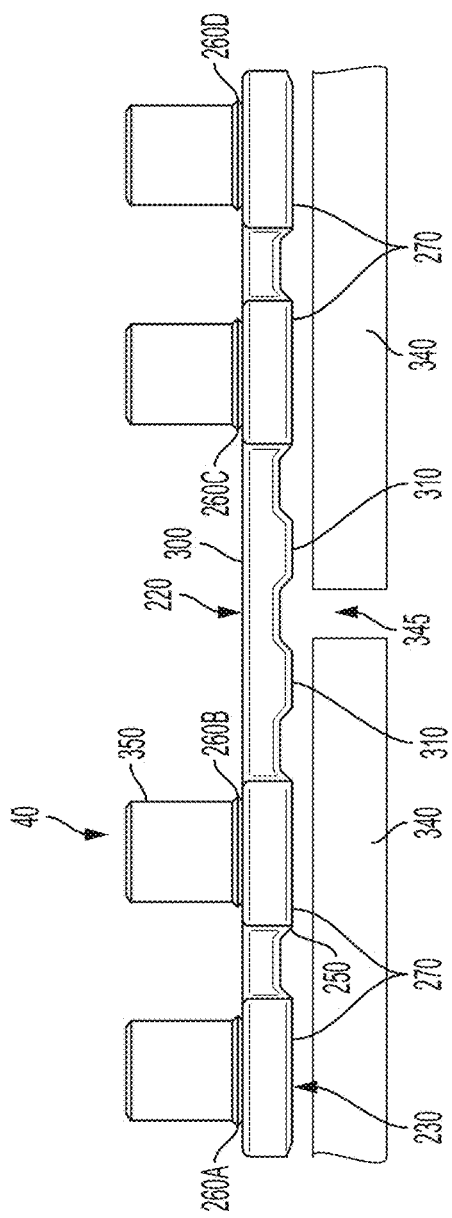
FIGS. 2G and 2H show an elevational view and perspective view, respectively, of the embodiment of the bone plate of FIG. 2A including attachment members.
Figure 2H:
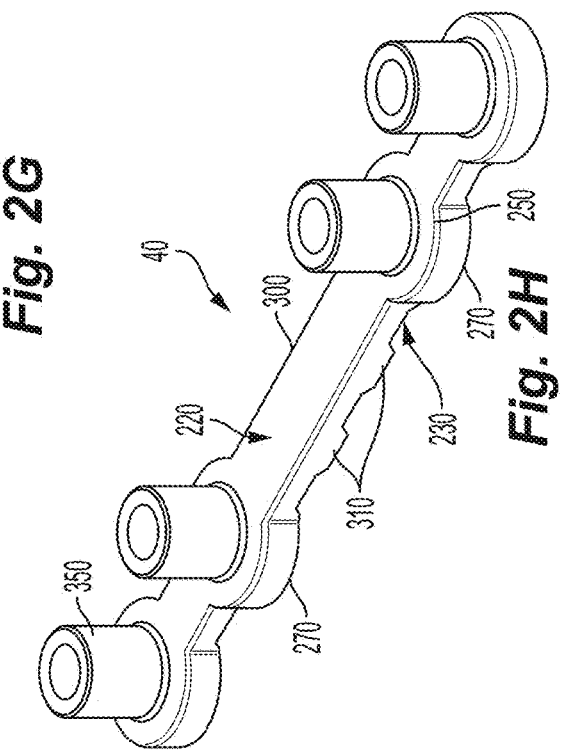

FIGS. 2G and 2H show a side elevational view and a perspective view, respectively, of the bone plate 40. Although the bone plate 40 is referenced for illustrative purposes here, this discussion can apply to all bone plate embodiments of various shapes. In FIG. 2G, the bone plate 40 has been positioned such that the bone facing surface 230 is facing a bone 340. As the bone plate 40 is moved closer to the bone 340, the pads 270 and 310 can come into contact with the bone 340. Contacting the bone 340 with the pads 270 and 310, as opposed to contacting the bone 340 with the bone facing surface 230 in general, can help to decrease trauma to the periosteal membrane of the bone 340 to allow for increased blood flow for healing. The bone plate 40 may also be positioned such that the bridge 300 extends across a target area 345. In the illustration of FIG. 2G, the target area 345 is depicted as a fracture of the bone 340. However, in other applications positioning the bridge 300 across the target area 345 may include positioning the bridge 300 across a joint between two bones, such as a metatarsal-cuneiform joint, or across other areas needing bone fixation at adjacent locations. Positioning the bridge 300 of the bone plate 40 across the target area 345 can help increase the strength and healing of the bone 340.

The bone plate 40 as shown has attachment members 350 configured at least partially within the fixation holes 260A, 260B, 260C, and 260D. For example, where the fixation holes 260A, 260B, 260C, and 260D are threaded, the attachment members 350 can also be threaded so as to be attached within the fixation holes 260A, 260B, 260C, and 260D. The attachment members 350 can be utilized, for example, to assist in locating and aligning various surgical tools and reamers and/or bending the bone plate 40 to better align with a contour of the bone 340 or other anatomy. For instance, it may be necessary to bend the bone plate 40 so that each of the pads 270 and 310 is in contact with the bone 340. The attachment members 350 can be, for example, cylindrical along an axial length of the members 350 and include apertures that are aligned with the respective fixation holes 260A, 260B, 260C, and 260D. As shown, the attachment members 350 have an elongated aperture, relative to the fixation holes 260A, 260B, 260C, and 260D, that can help align tools and/or drill bits used during various applications of the bone plate 40 in surgical procedures. Also, the extension of the attachment members 350 out from the top surface 220 can allow for greater leverage for bending the bone plate 40.

Although bone plate 40 can have a variety of different configurations, in some applications, the bone plate has a helical curvature extending between opposed fixation holes. The helical curvature can cause fixation hole(s) positioned in a distal section of the bone plate to be positioned in a different plane than fixation holes(s) positioned in a proximal section of the bone plate. For example, the helical curvature may follow a path traced along an imaginary cylinder or cone at an oblique angle so as to define a spiral or curved fold. In some examples, the angle and/or extent of curvature may be formed or adjusted in-situ by fabricating the bone plate out of a malleable material. The helical curvature of the bone plate may be configured to extend from the plantar region of a first metatarsal to the medial region of a medial cuneiform, thereby positioning the curvature across a metatarsal-cuneiform joint.

Figure 2I:
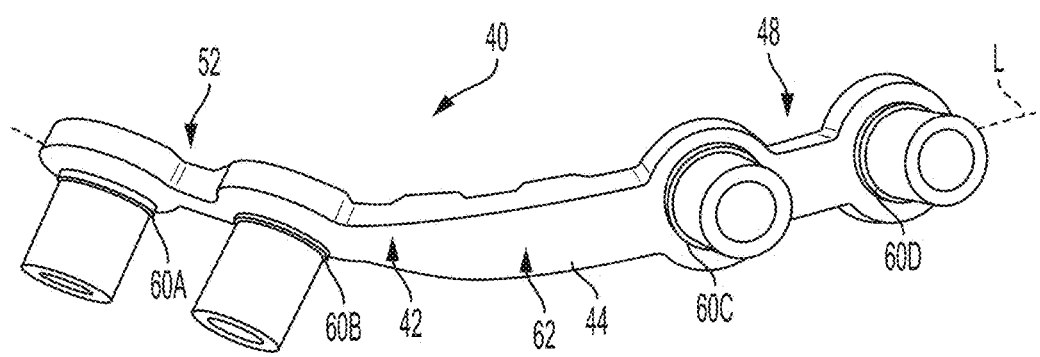
FIGS. 2I and 2J illustrate different perspective views of an example bone plate having a helical curvature.
Figure 2J:
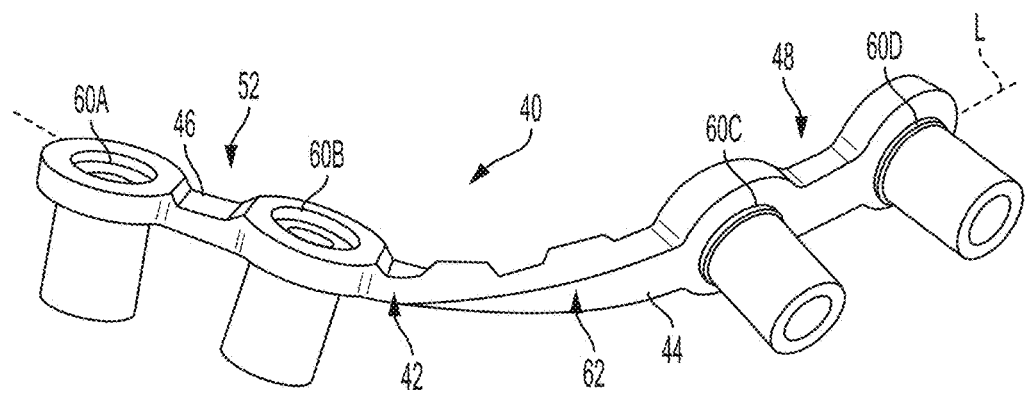

FIGS. 2I and 2J illustrate different perspective views of an embodiment of bone plate 40 that can be included in kit 10, where the bone plate has a helical curvature. As shown, the bone plate 40 defines a body 42 having a top surface 44 and a bone facing surface 46, where the bone facing surface 46 is on a side of the body 42 opposite the top surface 44. In an exemplary application, the bone plate 40 can be positioned so that the bone facing surface 46 interfaces with and/or is in contact with a bone. In the example shown in FIGS. 2I and 2J, the bone facing surface 46 includes multiple surfaces projecting different distances away from top surface 44. Thus, for convenience, "bone facing surface" will refer to the side of the bone plate generally facing bone when the plate is positioned on a bone, regardless of whether there is more than one surface and regardless of whether each surface is in contact with the bone when bone plate 40 is applied.

The body 42 of the bone plate 40 has a major length which defines the central longitudinal axis L. The body 42 can include a proximal region 48 at or near a first longitudinal end and a distal region 52 at or near a second longitudinal end that is opposite the first longitudinal end of the bone plate 40. The proximal region 48 may be separated from the distal region 52 by an intermediate region. For example, the body 42 may include one or more fixation holes. In these examples, body 42 may include one or more fixation holes in proximal region 48, one or more additional fixation holes in distal region 52, and an intermediate region devoid of fixation holes positioned between proximal region 48 and distal region 52.

In the illustrated embodiment, the distal region 52 has at least one fixation hole, which is illustrated as two fixation holes 60A and 60B, and the proximal region 48 has at least one additional fixation hole, which is illustrated as two fixation holes 60C and 60D. In other examples, body 42 may include fewer fixation holes (e.g., one, none) or more fixation holes (e.g., three, four) in proximal region 48 and/or distal region 52. Moreover, the dimensions (e.g., length) of the proximal and distal regions 48, 52 can be adjusted to accommodate the particular number of fixation holes included.

In the example shown, the proximal region 48 extends longitudinally from the first longitudinal end of the bone plate 40 to an end of the fixation hole 60C on the axis L furthest from the first longitudinal end. In addition, in this example, the distal region 52 extends longitudinally from the second longitudinal end of the bone plate 40 to an end of the fixation hole 60B on the axis L furthest from the second longitudinal end. Thus, in the illustrated example, the bone plate 40 includes a region between proximal region 48 and distal region 52, specifically between the terminal edge of fixation hole 60B and the terminal edge of fixation hole 60C, which is devoid of fixation holes and is sometimes referred to herein as a "bridge."

As shown in FIGS. 2I and 2J, the body 42 of the bone plate 40 can include a helical curvature 62. Such a helical curvature can include a curve that resides in three-dimensional space. In some embodiments, the distal region 52 lies in a first plane and the proximal region 48 lies in a second plane different from, and offset from, the first plane both along and about the longitudinal axis L. Depending on the extent of the bend and/or twist of the helical curvature 62 desired for a particular application, the first plane including the distal region 52 and the second plane including the proximal region 48 can be substantially perpendicular about the longitudinal axis. In some embodiments, the radius of the helical curvature can vary as a function of longitudinal position on the body 42. In other embodiments, the radius of the helical curvature can be constant as a function of longitudinal position on the body 42.

In the embodiment of the bone plate 40 shown in FIGS. 2I and 2J, the helical curvature 62 includes both a bend along the central longitudinal axis L (e.g., around an axis perpendicular to axis L) and a twist about the axis L. The bend may curve the proximal region 48 of the body 42 back toward the distal region 52 of the body about an intermediate bridge section between regions 55B and 55C. For example, the bend can reduce the distance between opposite end of body 42 as compared to when body 42 is flat or planar. The radius of the bend can vary or be constant as a function of longitudinal position on the body 42, and/or be concentrated in one or more portions of the body 42, such as the portion of the body between the proximal and distal portions. In some examples, the bend ranges from approximately 10° to approximately 45°, such as from approximately 15° to approximately 35°. In other examples, the bend ranges from 45° to 135°, such as from approximately 75° to approximately 105°. Other angles of bend are also possible.

The twist of helical curvature 62 about longitudinal axis L can rotate the proximal region of body 42 relative to the distal region 52 about axis L. For example, the twist may rotate regions 55C and 55D relative to regions 55A and 55B such that regions 55C and 55D, and the corresponding fixation holes defined therein, are radially offset from regions 55A and 55B, and the corresponding fixation holes defined therein. In some embodiments, the twist is concentrated in one or more portions of the body 42, such as the portion of the body between the proximal and distal portions. Further, in some examples, the twist of the body 42 ranges from approximately 45° to less than 180° about the axis L, such as from approximately 60° to approximately 100° about the axis L, or from approximately 70° to approximately 90° about the axis L. In other examples, the twist of the body 42 ranges from 25° to 100°, such as from 35° to 65°. Other angles of twist are also possible depending on the application.

While the bone plate 40 is described as having helical curvature 62, it should be appreciated that the curvature provided by the bone plate need not be a mathematically perfect helix. Rather, the helical curvature 62 may be a generally helical shape, such as a shape that follows the general contours of a helix even if the angles of contortion do not form a perfect helix. Therefore, it should be appreciated that a bone plate described as having a helical curvature according to the disclosure may, in practice, have a generally helical shape without forming a mathematically perfect helix. Additional bone plate details can be found in U.S. patent application Ser. No. 14/990,368, filed Jan. 7, 2016, the entire contents of which are incorporated herein by reference.

In some embodiments, the helical curvature 62 can be concentrated or entirely within a region of the body 42 between the proximal region 48 and distal region 52. Thus, any bend of the body 42 along the axis L and any twist of the body 42 about the axis L of the helical curvature 62 can begin at or near an end of the distal region 52 (e.g., begin at or adjacent fixation hole 60B) and proceed in a proximal direction toward the proximal region 48 (e.g., terminating at or adjacent fixation hole 60C). For instance, the helical curvature 62 (e.g., the bend along the axis L and the twist about the axis L) of the illustrated embodiment begins at the end of the distal region 52 and ends at the beginning of the proximal region 48. Thus, the helical curvature 62 as shown is located on a bridge portion of the body 42 between the fixation holes 60B and 60C. In such embodiments, the helical curvature 62 provides the transition of the body 42 from the first plane to the second plane. Moreover, in this embodiment, fixation holes 60A and 60B are positioned in the same plane, fixation holes 60C and 60D are also positioned in the same plane, and the plane fixation holes 60A and 60B are positioned in is offset from the plane fixation holes 60C and 60D are positioned in by helical curvature 62.

The helical curvature 62 can be included on the bone plate 40 so as to provide a twist and/or bend suitable for a particular application, e.g., such as facilitating positioning of the bone plate across a tarsal-metatarsal joint. In some examples, helical curvature 62 includes a twist of approximately 90° about the longitudinal axis of a bone (and the axis L of the bone plate 40). The helical curvature 62 also includes a bend along the axis L of the bone plate 40.

In some embodiments, the helical curvature 62 of the bone plate 40 is pre-formed, such that the bone plate includes the helical curvature when it is removed from kit 10. For example, helical curvature 62 may be formed in bone plate 40 before placing in kit 10, and the bone plate may be sufficiently rigid to hold the helical curvature until use. In some additional embodiments of the bone plate 40, body 42 can include malleable materials that allow for in-situ bending of the helical curvature 62. In still other embodiments, the bone plate may contain a pre-formed helical curvature 62 yet be formed of malleable materials such that the bone plate can be further bent during a surgical procedure. This can allow a clinician to adjust the radius of curvature and/or amount of bend of helical curvature 62 during a procedure to best fit the particular anatomy and/or patient undergoing the procedure (e.g., depending on the dimensions of the bones to which the bone plate 40 is to be fixed). For example, a clinician may remove the bone plate 40 from kit 10 and then bend the bone plate between proximal region 48 and distal region 52 until the shape of the helical curvature 62 best matches the anatomy across which the bone plate 40 is being positioned. In applications where bone plate 40 includes a pre-formed helical curvature 62, the amount of bending provided by the clinician may range from plus 20° (making the body 42 flatter) to minus 20°, such as from plus 10° to minus 10°, or from plus 5° to minus 5°, although other degrees of bending may also be used depending on the application.

In some embodiments, the kit 10 includes at least one and no more than four bone plates 40, with the exact number of bone plates 40 included in the kit 10 varying depending on the specific surgical procedure for which the kit 10 is configured to be used. For example, in some surgical procedures the bone plates are aligned with respect to the bone such that they reside in different planes. For example, two bone plates can be attached to a bone with the two bone plates positioned about 90 degrees, with respect to each other, along the outer circumference of the bone (e.g., left side and top, or top and right side). In certain surgical procedures, the longitudinal axes of the bone plates can be substantially parallel. This can, for instance, be beneficial for providing a strong fixation with respect to more than one plane.

Figure 3:
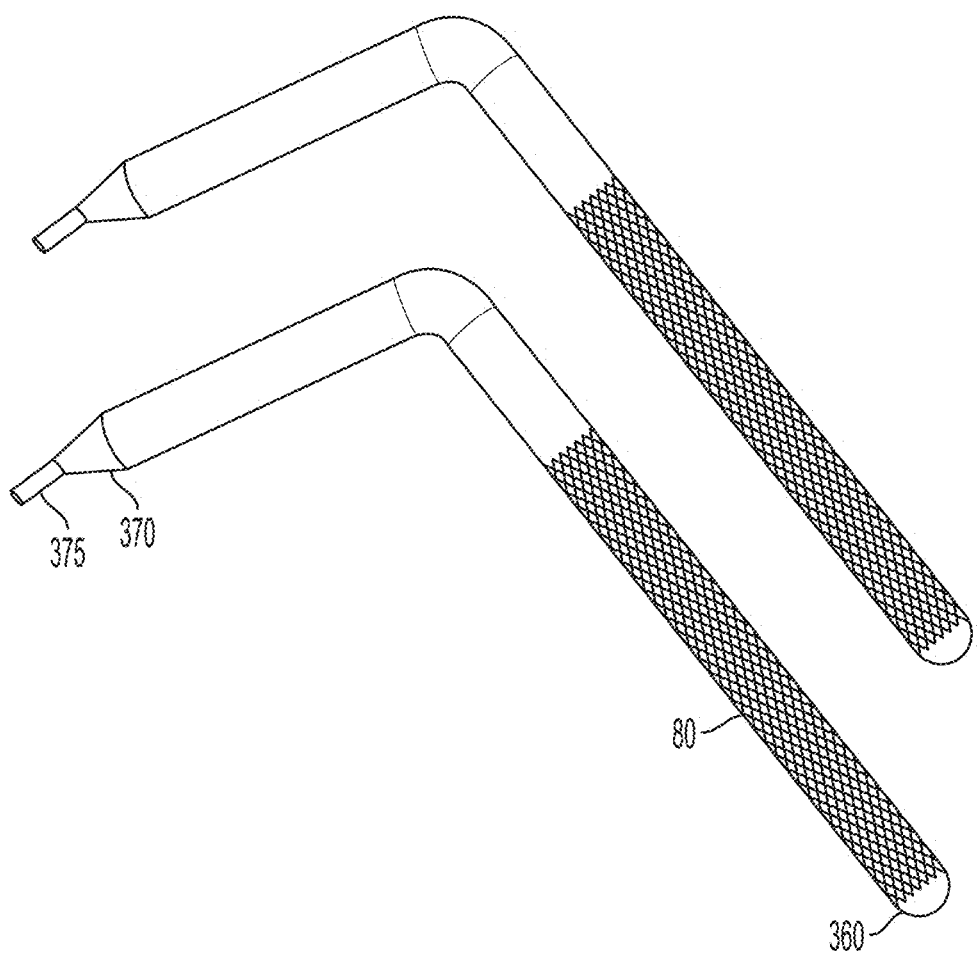
FIG. 3 is a perspective view of one embodiment of plate manipulation instruments.

FIG. 3 shows a perspective view of the embodiments of the plate manipulation instruments 80 shown and described as included in the kit 10 with respect to FIG. 1. The plate manipulation instruments 80 can have a first end 360 and a second end 370. In the illustrated embodiment, the first end 360 is at an angle relative to the second end 370. At least a portion of the first end 360 can include a friction surface so as to facilitate, for example, gripping at or near the first end 360 by, for example, a surgeon. The second end 370 may be configured so as to be insertable within the attachment member 350 (shown, e.g., in FIG. 2G). Where attachment members 350 are not present, the second end 370 may be configured so as to be insertable within the fixation holes 260A-D (shown, e.g., in FIG. 2B) of the bone plate 40. Inserting the second end 370 into the attachment member 350 (or fixation holes 260A-D) can allow the bone plate 40 to be bent or otherwise altered in geometry so as to substantially match a contour of a bone to which the bone plate 40 is to be fixed. The angle at which the second end 370 is disposed with respect to the first end 360 can facilitate bending the bone plate 40 by providing leverage complimentary to the force applied at the gripped first end 360.

In addition to the second end 370 being configured so as to alter the geometry of the bone plate 40, the second end 370 can also be configured so as to drive one or more of the bone plate fasteners 60. This can allow the kit 10 to be more compact where desired. For example, the second end 370 may include a tip 375 that is configured to mate with the head 160 of the bone plate fastener 60. As such, the tip 375 can be used to drive the bone plate fastener 60 received within one of the fixation holes 260A-D into a bone. In addition, in some embodiments, the tip 375 can be configured so as to drive one or more of the external fasteners 150 into a bone at a location spaced from the bone plate 40. Further, the tip 375 may be configured to mate with the attachment members to rotationally connect or remove the attachment members from the bone plate.

Figure 4:
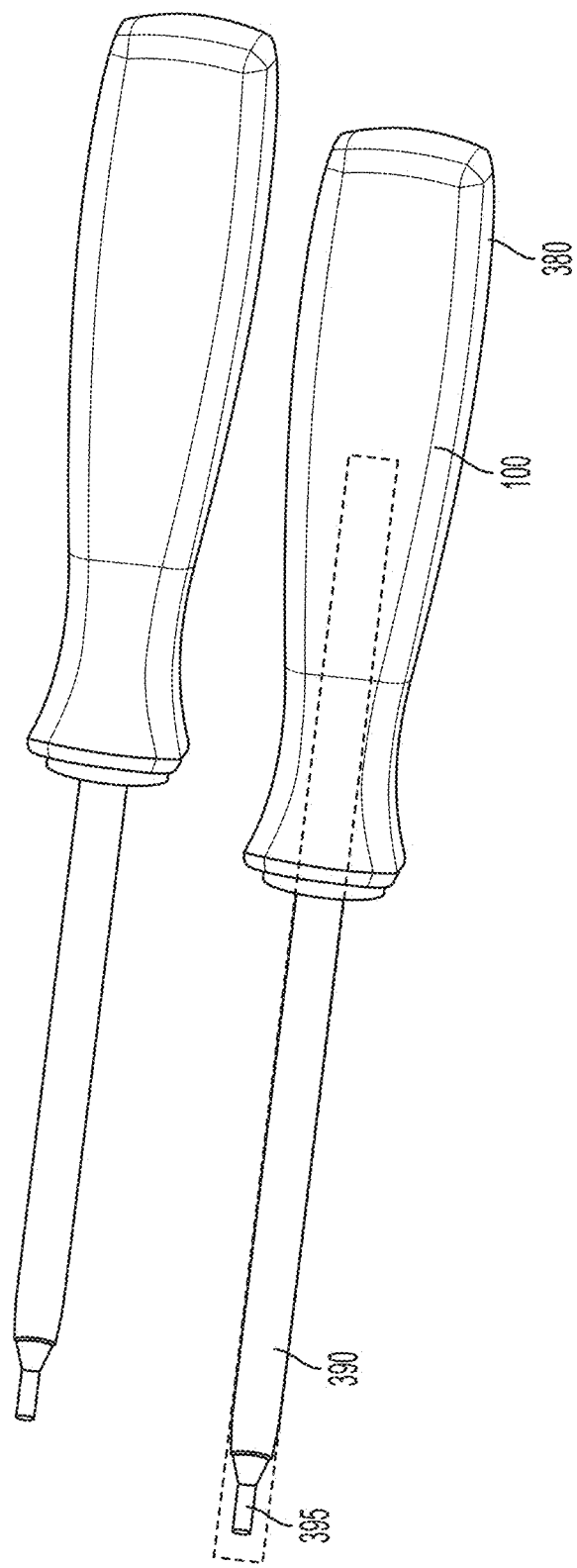
FIG. 4 is a perspective view of an embodiment of a driver member that can also serve as a plate manipulation instrument.

FIG. 4 shows a perspective view of the embodiments of the driver members 100 shown and described as included in the kit 10 with respect to FIG. 1. The driver members 100 can have a first end 380 and a second end 390. The driver member 100 can be gripped at or near the first end 380, while the second end 390 can be configured so as to mate with the head 160 of the bone plate fastener 60 and/or the head 180 of the external fastener 150, for instance, via a tip 395. As a result, the driver member 100 can be used to drive the bone plate fastener 60 received within one of the fixation holes 260A-D into a bone to fixate the bone plate 40 and/or drive the external fastener 150 into a bone (at a location spaced from the bone plate 40) to fixate the bone. In embodiments where the plate manipulation instrument 80 is not included in the kit 10, the driver member 100 can also be used to bend the bone plate 40 similar to that described for the plate manipulation instrument 80. Further, the tip 395 may be configured to mate with the attachment members to rotationally connect or remove the attachment members from the bone plate. This may allow the kit 10 to be more compact.

Figure 5:
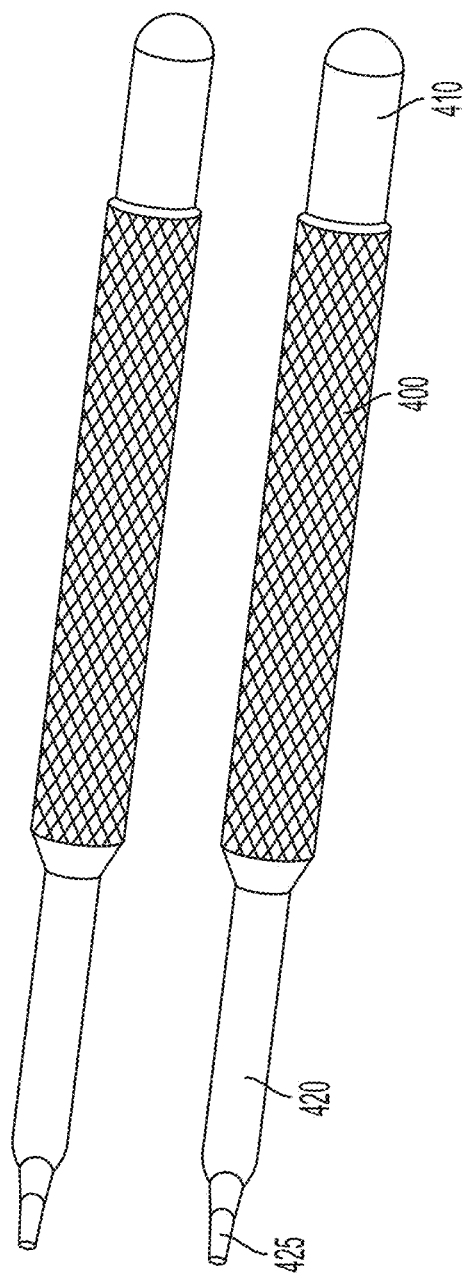
FIG. 5 is a perspective view of another embodiment of a driver member that can also serve as a plate manipulation instrument.

FIG. 5 shows a perspective view of an alternative embodiment of driver members 400. Instead of the driver member 100, the kit 10 may instead include at least one and no more than three driver members 400. Similar to the driver members 100, the driver members 400 can have a first end 410, at or near which the driver member 400 can be gripped, and a second end 420 configured so as to mate with the head 160 of the bone plate fastener 60 and/or the head 180 of the external fastener 150, for instance, via a tip 425. Additionally, where the plate manipulation instrument 80 is not included in the kit 10, the driver member 400 can also be used to bend the bone plate 40 similar to that described for the plate manipulation instrument 80. Further, the tip 425 may be configured to mate with the attachment members to rotationally connect or remove the attachment members from the bone plate.

Figure 6:
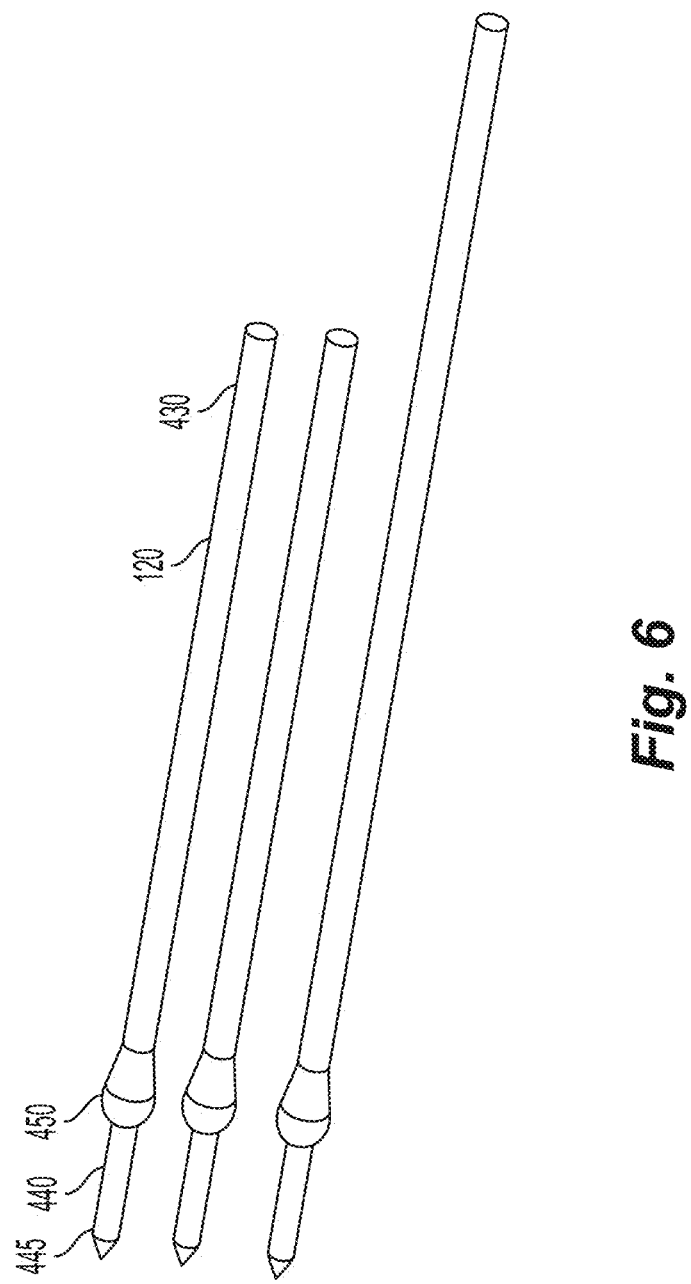
FIG. 6 is a perspective view of one embodiment of bone cut pins.

FIG. 6 illustrates a perspective view of the bone cut pins 120 shown and described as included in the kit 10 with respect to FIG. 1. The bone cut pins 120 may have a first end 430 and a second end 440 having an end portion that can include a point 445, which may be fluted for cutting bone. In one application, the bone cut pin 120 can have the point 445 inserted through one fixation hole 260A-D of the bone plate 40 so as to contact the bone. The point 445 may be used to create an initial pilot hole in the bone at a location aligned with the fixation hole 260A-D. This initial pilot hole can then be used as a location where the bone plate fastener 60 is to be fixed to the bone after being received in the fixation hole 260A-D. Furthermore, the bone cut pins 120 can be of varying lengths. As illustrated, one of the bone cut pins 120 is longer than the others. The difference in length of the bone cut pins 120 can serve to prevent interference caused by the ends 430 to other surgical instruments used in a similar or proximate location.

A collar, sometimes referred to as an olive 450, can be included on the bone cut pin 120 at a location spaced from the point 445 as well as the second end 440. The collar 450 can have a diameter greater than a diameter of the point 445, and it can act as a depth gauge structure. As a result of the larger diameter of the collar 450 relative to the point 445, the tip 445 and end 440 cannot be inserted into the bone any further than the surface of the collar 450 nearest the end 440. Thus, the collar 450 can serve as a stopping point along a longitudinal axis of the bone cut pin 120. As such, the exact location of the collar 450 on the bone cut pin 120 can vary depending on the desired depth of penetration of the end 440 into the bone. Additionally, the collar 450 can serve as means to measure a depth of penetration of the tip 445 into the bone while creating the initial pilot hole.

Figure 7:
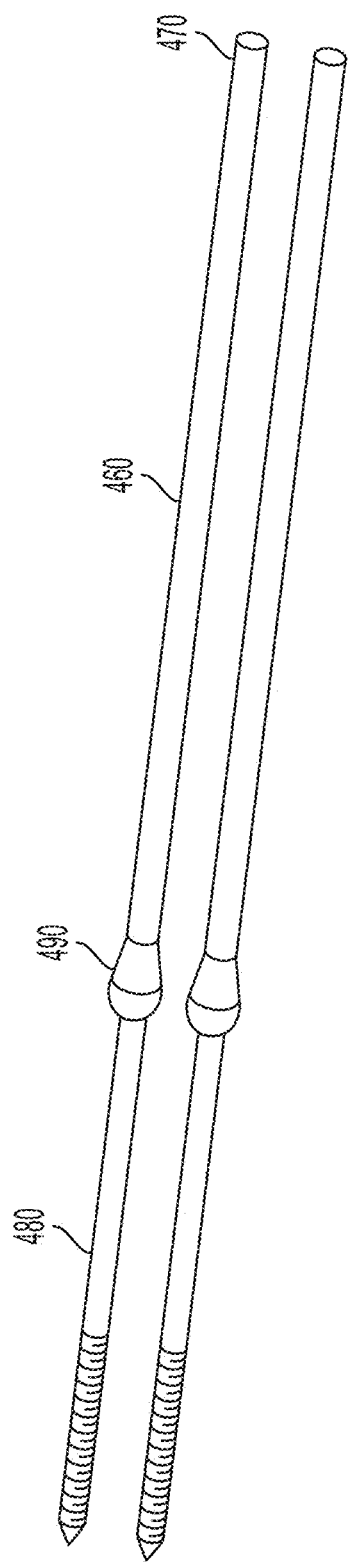
FIG. 7 is a perspective view of one embodiment of bone fixation pins.

FIG. 7 shows a perspective view of bone fixation pins 460. Although not shown in the embodiment of the kit 10 described with respect to FIG. 1, at least one and no more than four bone fixation pins 460 can be included in various embodiments of the kit 10. Each bone fixation pin 460 can have a first end 470 and a second end 480 which may include a threaded portion as illustrated. A collar 490 can be included at a location on one or more of the bone fixation pins 460 spaced from the end 480 and serve a function similar to that described with respect to collar 450 of FIG. 6.

Bone fixation pins 460 can be used to fix one or more bones in a particular position as desired for a surgical procedure. The bone fixation pins 460 can be used to fix one or more bones independent of and at a location spaced from the bone plate 40. For instance, the threaded portion of the end 480 of one bone fixation pin 460 can be inserted into a bone in a manner that fixes the bone in the desired position. In some procedures, one or more additional bone fixation pins 460 can also be inserted into the same bone or one or more adjacent bones such that the one or more bones are appropriately fixed as desired. This can facilitate greater accuracy during a surgical procedure. For example, at least one bone fixation pin may be inserted into adjacent bones, crossing the joint space between the bones, and used to compress the bones together prior to the installation of a bone plate.

Figure 8:
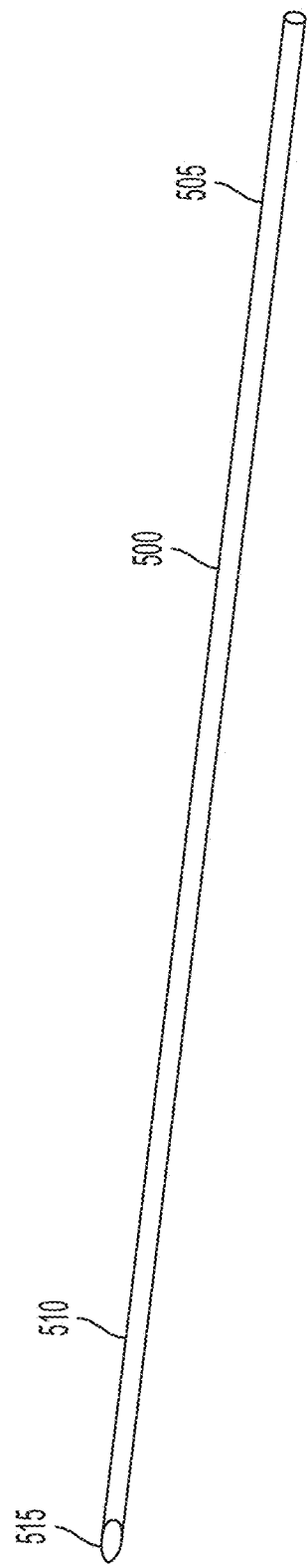
FIG. 8 is a perspective view of an embodiment of a single external fastener bone cut pin.

FIG. 8 illustrates a perspective view of an embodiment of a single external fastener bone cut pin 500. Although not shown in the embodiment of the kit 10 described with respect to FIG. 1, where an embodiment of the kit 10 includes the external fastener 150 (shown and described with respect to FIG. 2A) the kit 10 can further include the single external fastener bone cut pin 500 and no other external fastener bone cut pins. In embodiments where the external fastener has a diameter different than a diameter of a bone plate fastener, the single external fastener bone cut pin can be sized to accommodate the diameter of the external fastener. The external fastener bone cut pin 500 may have a first end 505 and a second end 510. At the second end 510 can be a point 515. The external fastener bone cut pin 500 can be used to create an initial pilot hole for the external fastener 150 via the point 515 at a location on a bone where the external fastener 150 is to be inserted.

In addition to the surgical items described previously, embodiments of the kit 10 may further include a bone preparation instrument that can be disposed after use on a single surgical patient. The bone preparation instrument can be useful during a surgical procedure to position and/or cut one or more bones. In some embodiments, the kits include only two or fewer (e.g., one) bone preparation instruments. Several embodiments of such instruments will be described in turn below.

FIGS. 9A and 9B show a first embodiment of a bone preparation instrument 520. FIG. 9A shows a perspective view of the bone preparation instrument 520 with some components shown in an exploded view, while FIG. 9B shows a perspective view of the bone preparation instrument 520 assembled. Additional discussion of exemplary instruments and techniques that can be included in, or used with, kit 10 are provided in U.S. patent application Ser. No. 14/981,335, filed Dec. 28, 2015, and 62/293,189, filed Feb. 9, 2015, the entire contents of which are incorporated herein by reference.

With reference to FIGS. 9A and 9B, the bone preparation instrument 520 can include a support 530 which defines an inner cavity 540. In one embodiment, the support 530 can include a first fixation aperture 550A and a second fixation aperture 550B, each of which can extend through the support 530 and receive bone preparation fixation pins 140A and 140B, respectively, such that the fixation pins 140A and 140B extend through the support 530 via the fixation apertures 550A and 550B. In the embodiment shown, the fixation pins 140A and 140B have a threaded first end adapted to threadingly engage with a bone, and allow the support 530 to be translated along a longitudinal axis of both pins 140A and 140B. In the illustrated embodiments, the fixation apertures 550A and 550B are located on opposite longitudinal ends of the support 530, but in other embodiments the fixation apertures 550A and 550B can be located at various positions on the support 530. The support 530 can further include one or more extensions 570A and/or 570B protruding generally radially out from the support 530, which may define a concave surface configured to receive a generally cylindrical bone portion. In the embodiment shown, fixation aperture 550B is provided with an extension member 572 which can be threadingly coupled to the support 530. Such an extension member 572 can be adjusted relative to the support 530 to allow the support to become parallel with a longitudinal axis of a bone, if desired. In such embodiments, the support 530 can rest on a bone via the extensions 570 A/B and extension member 572 in a position generally parallel to the bone. Fixation pin 140B may be received within an internal aperture of the extension member 572. Aperture 574A (and aperture 574B, not shown, on an opposite side of the support 530 from aperture 574A), such as tapered apertures, may be provided proximal to extension 570A (and 570B). Such apertures may extend through the support at a skewed angle relative to the longitudinal axis of the support, and may be used to engage a clamping instrument or receive fixation pins.

The support 530 can also include a slot 580 formed on at least a portion of a surface of the support 530. As illustrated in the embodiment of the bone preparation instrument 520 shown in FIG. 9B, the slot 580 can extend in a surface of the support 530 between fixation apertures 550A and 550B. A securing component 590 can be configured to translate along the slot 580 relative to the support 530. For example, the securing component 590 can have a first end with a diameter greater than a diameter of a second opposite end, such that the first end of the securing component 590 is supported by the slot 580 (i.e. the first end has a diameter greater than a radial width of the slot 580) while the second end of the securing component 590 is positioned within the slot 580 (i.e. the second end has a diameter less than a radial width of the slot 580).

The inner cavity 540 of the support 530 can have a shaft 600 positioned at least partially within the inner cavity 540. The shaft 600 can be configured so as to translate within the inner cavity 540 relative to the support 530, such that an end of the shaft 600 can be made to project out from the inner cavity 540. The shaft 600 may define a slot 605 which may be aligned with the slot 580 defined by the support 530. This slot 605 may receive the pin 140A to reduce interference when the shaft 600 translates. Furthermore, the shaft 600 can include a securing aperture 610 which can be configured to receive at least a portion of the securing component 590. In one embodiment, both the second end of the securing component 590, within the slot 580, and the securing aperture 610 can be threaded to allow the securing component 590 to mate with the securing aperture 610. Such a configuration can allow the shaft 600 to be fixed, such as by compressing a surface of the support 530 that defines the slot 580, and thus prevented from translating within the inner cavity 540, relative to the support 530. In another embodiment, the securing component 590 can be threadingly engaged with the support 530 to act against the shaft 600 to prevent the shaft 600 from traveling with the cavity 540 when desired.

On an end of the shaft 600, a main guide member 620 can be disposed. In some embodiments the main guide member 620 can be integral with the shaft 600, or in other embodiments the main guide member 620 and the shaft 600 can be separate components coupled together. The main guide member 620 can have a first guide surface 630A and a second guide surface 630B, and in some embodiments the main guide member 620 can include blocks 640A and/or 640B. The first and second guide surfaces 630A and 630B can be adjacent surfaces facing one another with a space defined between the first and second guide surfaces 630A and 630B. For example, the first guide surface 630A can be a surface of the main guide member 620 immediately opposite a surface of the main guide member 620 that interfaces with the shaft 600, and the second guide surface 630B can be a surface of the main guide member 620 immediately opposite a surface of the main guide member 620 that includes blocks 640A and 640B. In the illustrated embodiment, the second guide surface 630B contains a gap, such that the second guide surface 630B is not a single, continuous surface. In other embodiments, the second guide surface 630B can be a single, continuous surface lacking any such gap. The first guide surface 630A defines a first plane, while the second guide surface 630B defines a second plane. As shown, the first guide surface 630A and the second guide surface 630B can be configured such that the first plane is parallel to the second plane, with the space between. In further embodiments (not illustrated), the guide surfaces 630A and 630B can be configured such that the first and/or second planes are skewed.

As previously noted, a surface of the main guide member 620 can include one or more blocks 640A and 640B, either integral with the main guide member 620 or as separate components attached to the main guide member 620. As shown, the blocks 640A and 640B can be on a surface on a side of the main guide member 620 furthest from the interface with the shaft 600. In other applications, the blocks 640A and 640B can be located at various other positions on the main guide member 620. The blocks 640A and 640B can include fixation apertures 650A and 650B respectively. The fixation apertures 650A and 650B extend through the blocks 640A and 640B and provide a location for configuring additional fixation pins (e.g. bone fixation pins 460 shown in, e.g., FIG. 7) to, for example, position a bone or bones.

In addition to the support 530, the bone preparation instrument 520 can include a bridge component 660. As shown in FIG. 9B, the bridge component 660 can attach to the main guide member 620. In particular, in some applications of the bone preparation instrument 520 the bridge component 660 can have a geometry that allows the bridge component 660 to attach to the main guide member 620 between the first and second guide surfaces 630A and 630B through an interference fit. Optionally, a locking mechanism can be provided to lock the bridge component to the main guide member, such as a locking tab, screw, pin, cam, etc. For example, the bridge component 660 may have a planar member 665 (shown in FIG. 9A) that is received within the gap between the surfaces 630A and 630B and an extending block 666 (shown in FIG. 9A) adapted to extend into the surface gap of 630B. In other applications, the bridge component 660 can be coupled to the main guide member 620 by any attachment mechanism, such as screws or clamps. The bridge component 660 can include rails 670A and 670B, each extending out from the bridge component 660 in a same general direction. In other embodiments, the rails 670A and 670B can extend out from the bridge component 660 at different angles.

The bone preparation instrument 520 can also include in some embodiments a fixating structure 680. The fixating structure 680 can be supported on the rails 670A and 670B. For example, the fixating structure 680 can include apertures 685A and 685B to receive the rails 670A and 670B, respectively. The fixating structure 680 can be secured to the rails 670A and 670B, such that the fixating structure 680 is obstructed from translating along the rails 670A and 670B, by turning or otherwise actuating an actuator 686 of the fixating structure 680, which moves a lock (not shown) to act against the rails. Furthermore, the fixating structure 680 can also include one or more fixation apertures 690A and/or 690B. Fixation apertures 690A and 690B extend through fixating structure 680 and can be located on opposite ends of the fixating structure 680, at a skewed angle, and serve to receive fixation pins or other means for stabilizing the bone preparation instrument 520 across a targeted anatomy and/or positioning a bone or bones.

Additionally, the bone preparation instrument 520 can have a secondary guide member 700. The secondary guide member 700 can be supported on the rails 670A and 670B. For example, the secondary guide member 700 may include slots 705A and 705B to receive the rails 670A and 670B such that the secondary guide member 700 is supported thereon. The secondary guide member 700 can also have a third guide surface 710A and a fourth guide surface 710B. The third and fourth guide surfaces 710A and 710B can be adjacent surfaces facing one another with a space defined between the third and fourth guide surfaces 710A and 710B. In the illustrated embodiments, third and fourth guide surfaces 710A and 710B are single, continuous surfaces that do not include a gap, but in other embodiments third and/or fourth guide surfaces 710A and 710B can include a gap. The third guide surface 710A defines a third plane, while the fourth guide surface 710B defines a fourth plane. As shown, the third guide surface 710A and fourth guide surface 710B can be configured such that the third plane is parallel to the fourth plane, with the space between. In further embodiments (not illustrated), the guide surfaces 710A and 710B can be configured such that the third and/or fourth planes are skewed. Further, the third and/or fourth guide surfaces may be parallel to or skewed with respect to the first and/or second guide surfaces, such that the cutting guide can be adapted to make parallel cuts or angular cuts or cut shapes (e.g. a chevron shape). In some embodiments, the secondary guide member 700 can be locked to the rails 670A and/or 670B with a locking screw, cam, pin, etc.

In one application, the secondary guide member 700 can be supported on the rails 670A and 670B at a location along the rails 670A and 670B between the fixating structure 680 and the main guide member 620. Additionally shown in FIG. 9B are bone preparation fixation pins 140C and 140D received within fixation apertures 690A and 690B such that the fixation pins 140C and 140D extend through the fixating structure 680. In some applications of the bone preparation instrument 520, it may be desirable to provide the fixation pins 140C and 140D at an angle other than 90 degrees relative to a top surface of the fixating structure 680 by configuring the fixation apertures 690A and 690B to extend through the fixating structure 680 at a skewed angle to guide the fixating pins 140C and 140D. Fixation pins 140C and 140D can be used, for example, for stabilizing the bone preparation instrument 520 across a targeted anatomy and/or positioning a bone or bones.

Embodiments of the bone preparation instrument 520 can be useful in a surgical procedure for temporarily positioning a bone or bones and guiding a cutting of a bone or bones at a targeted anatomy. Bone cutting can be useful, for instance, to facilitate contact between leading edges of adjacent bones, separated by a joint, or different portions of a single bone, separated by a fracture, such as in a bone alignment and/or fusion procedure. Cuts can be made to bone with respect to the bone positioning instrument, and the bones can be positioned for an additional surgical step, such as bone plating, after the cuts have been made. As such, the bone preparation instrument 520 can be used in methods for temporarily fixing an orientation of a bone or bones, such as during a surgical procedure, and guiding cutting at desired bone locations.

The support 530 is placed on the bone. For embodiments of the bone preparation instrument 520 that include the extensions 570A and 570B, the extensions 570A and 570B can be used to at least partially straddle the bone and consequently provide both greater stability to the support 530 on the bone and anatomical alignment of the support 530 on a longitudinal axis of the bone (e.g., the slot 580 is generally parallel to the longitudinal axis of the bone). Extension member 572 can be adjusted to a desired distance from support 530. Further, in some embodiments it can be desirable to align and fix the support 530 along the longitudinal axis of the bone using the fixation pins 140A and 140B. The pin 140A can be inserted through the fixation aperture 550A such that an end of the pin 140A protrudes out from the fixation aperture 550A adjacent the bone. The pin 140A can then be fixed to the bone. Similarly, the pin 140B can be inserted through fixation aperture 550B and fixed on an end to the bone. In this manner, the support 530 can be fixed in place to and aligned along the longitudinal axis of the bone.

In addition to fixing the support 530 to the bone, the main guide member 620 can be aligned such that the main guide member 620 is positioned at a location where a bone is to be cut. In one embodiment, the main guide member 620 can be positioned at the location where a bone is to be cut by appropriately positioning and fixing the support 530—the support 530 is fixed to the bone at a location along the bone that results in the main guide member 620 being positioned at the location where a bone is to be cut. In some embodiments, a joint alignment blade (not shown) is inserted though the main guide member and into a joint space to help align the main guide member in a desired position. Further, in certain embodiments, the bone fixation pin 460 can be inserted through a bone of interest and into an adjacent bone (e.g., though a first metatarsal and into a second metatarsal) to provide additional stability during the procedure.

However, in some applications a location of the main guide member 620 relative to the longitudinal axis of the bone can be adjusted without necessitating movement of the support 530. To accomplish this, the shaft 600 at least partially within the inner cavity 540 can be translated relative to the support 530 to cause the main guide member 620 to translate along the longitudinal axis of the bone a distance as a result of the shaft 600 being moved the same distance. Once the main guide member 620 is positioned at the location to be cut, the securing component 590 can be translated along the slot 580 such that the securing component 590 is aligned with securing aperture 610. The securing component 590 can then be fixed within the securing aperture 610 such that the shaft 600 is fixed relative to the support 530.

Once the main guide member 620 has been positioned at the location to be cut, a cutting member (e.g. a saw blade) can be inserted through the space defined between the first guide surface 630A and the second guide surface 630B to cut the bone. The guide surfaces 630A and 630B can serve to direct the cutting member to the location of the bone to be cut, which in many applications can be a precise location. The break or window defined in the second guide surface 630B can assist in visualizing the portion of the bone being cut.

In some embodiments, the main guide member 620 can be used to make additional cuts. In such embodiments, the securing component 590 can be loosened and the shaft 600 can be translated within the cavity to a desired position. The securing component 590 can be then be fixed within the securing aperture so the shaft is again fixed relative to the support 530. In some embodiments, fixation pins may be inserted through fixation aperture 650A and/or 650B and into the bone to further stabilize the main guide member 620. After the main guide member 620 has been repositioned at the location to be cut, a cutting member (e.g. a saw blade) can be inserted through the space defined between the first guide surface 630A and the second guide surface 630B to cut the bone.

As shown in FIG. 9B, once the bone has been cut the additional components of the bone preparation instrument 520 can be added. In certain surgical procedures, it may be desirable to use bone preparation instrument 520 to make a second cut the same or different bone as the first cut. The secondary guide member 700 can be used to facilitate this second cut by positioning the secondary guide member at the location where the second cut is to be made. A cutting member (e.g. a saw blade) can be inserted through the space defined between the third and fourth guide surfaces 710A and 710B to cut the bone. The guide surfaces 710A and 710B can serve to direct the cutting member to the location on the bone to be cut. As illustrated, the cut made using the secondary guide member 700 will be a cut that is generally parallel to the cut made using the main guide member 620. However, in other embodiments components of the bone preparation instrument 520 (e.g. rails 670A and 670B) can be configured such that the cut made using the secondary guide member 700 is an angular cut (i.e. not parallel) relative to the first cut made using the main guide member 620.

When the bone or bones have been cut and positioned as desired on the single surgical patient, the bone preparation instrument 520 can be removed and discarded using convention means.

Figure 10A:
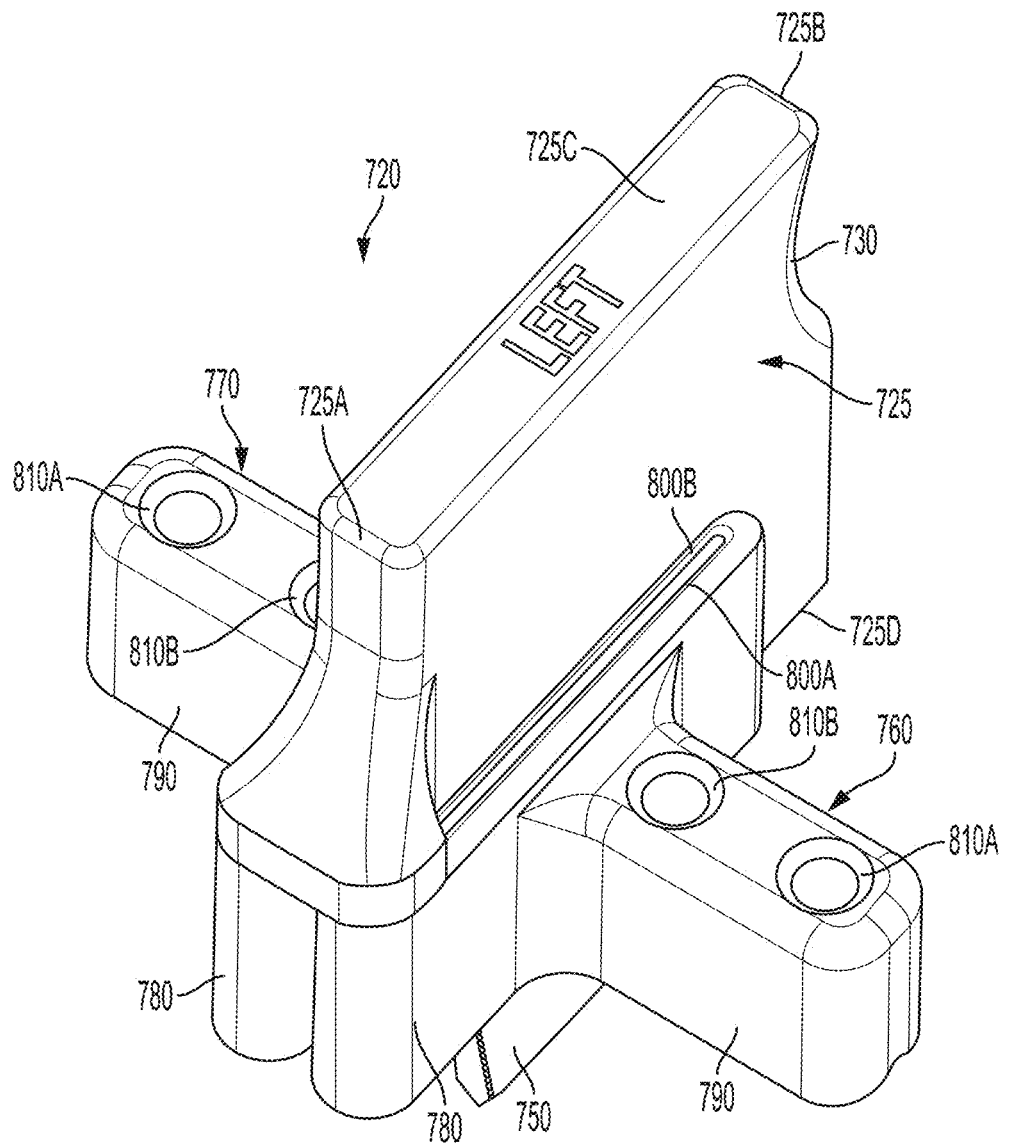
FIG. 10A a perspective view of a second embodiment of a bone preparation instrument.
Figure 10B:
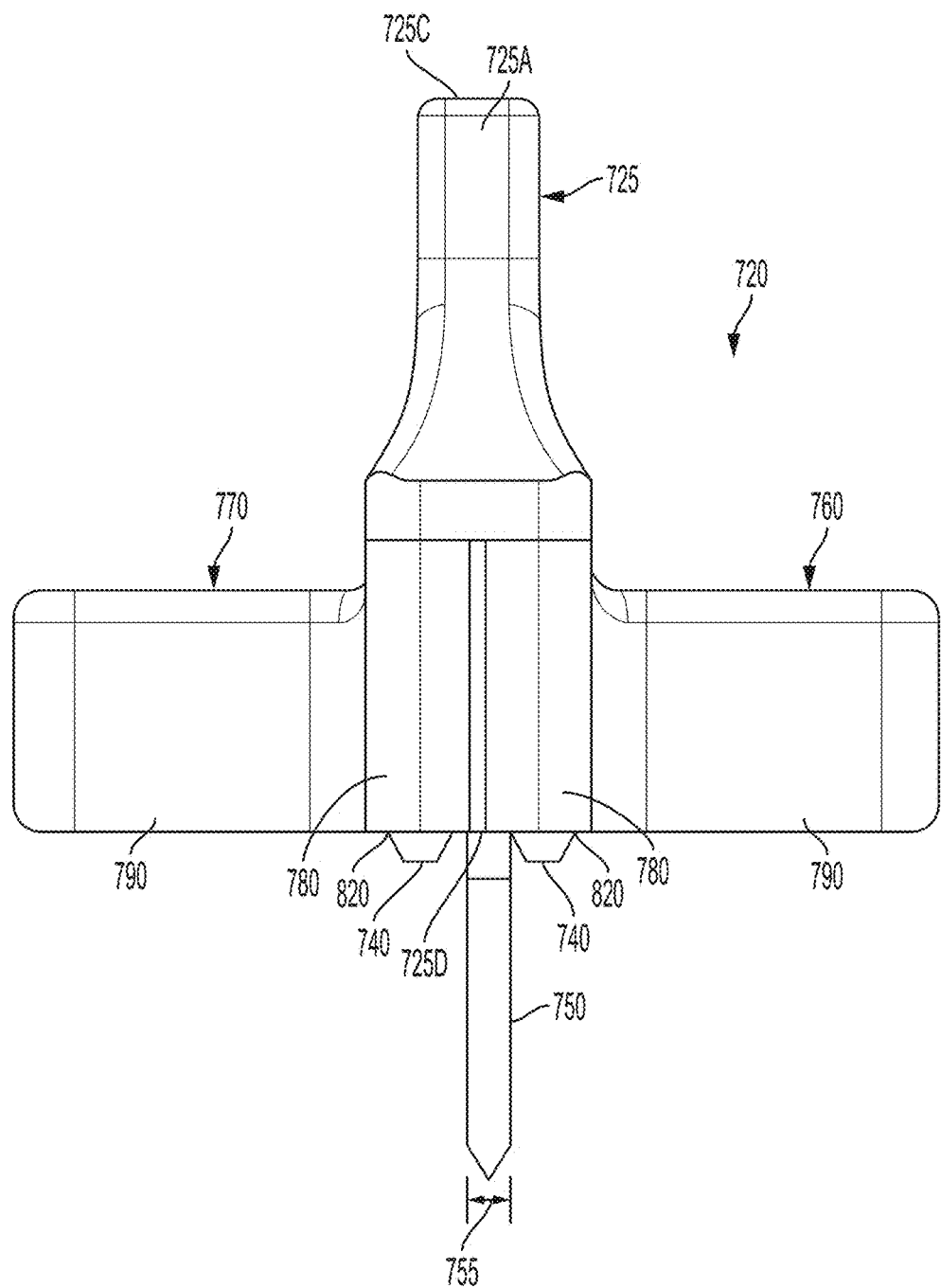
FIG. 10B is a side elevational view of the bone preparation instrument of FIG. 10A.
Figure 10C:
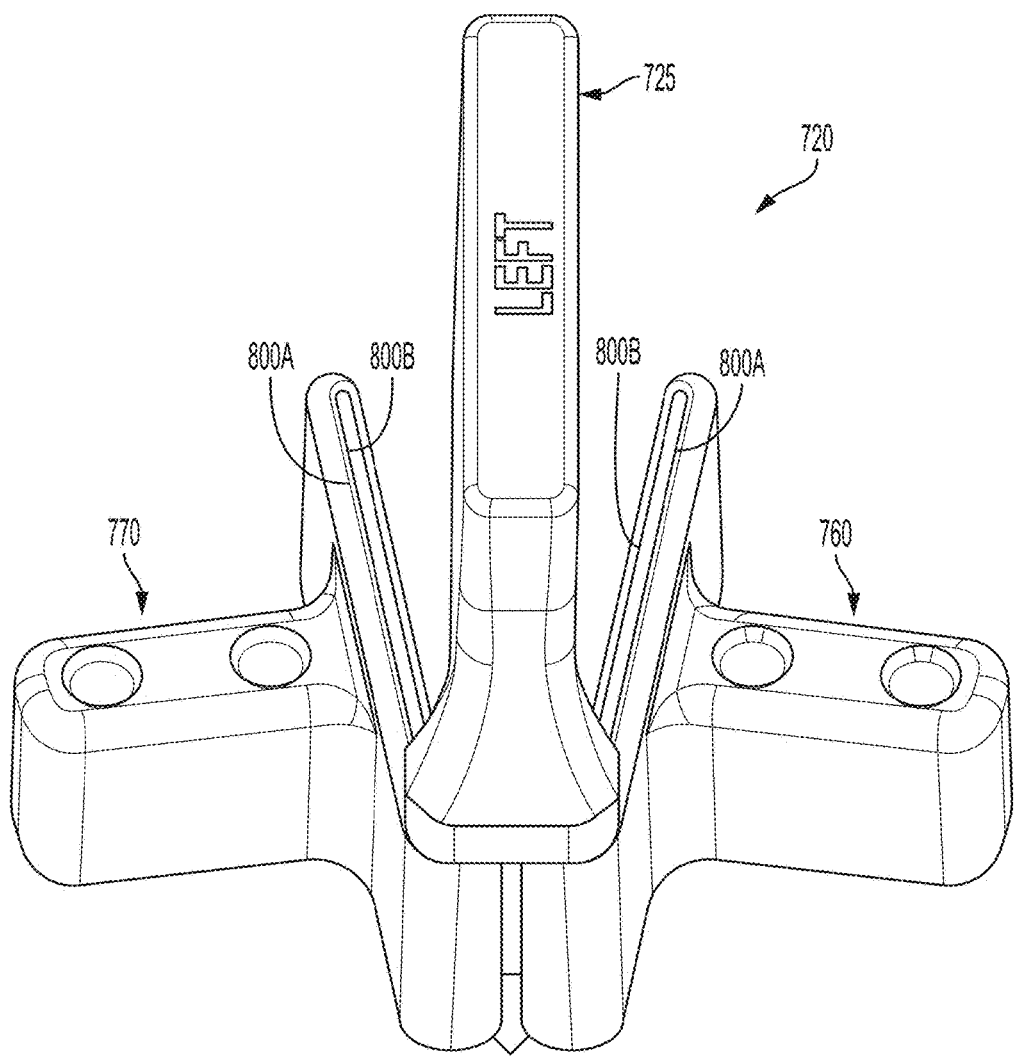
FIG. 10C is a perspective view of the bone preparation instrument of FIG. 10A showing guide members of the bone preparation instrument aligned at a skewed angle relative to a block of the bone preparation instrument.

FIGS. 10A-C illustrate a second embodiment of a bone preparation instrument 720. The bone preparation instrument 720 can serve as a single bone preparation instrument included in embodiments the kit 10 and be disposed after use on a single surgical patient. FIG. 10A shows a perspective view of the bone preparation instrument 720, FIG. 10B shows a side elevational view of the bone preparation instrument 520, and FIG. 10C shows another perspective view of the bone preparation instrument 520.

The bone preparation instrument 720 can include a block 725 having first and second side ends 725A and 725B as well as a top end 725C and a bottom end 725D. The block 725 can be made, for example, from a polymeric material. In the illustrated embodiment, the block 725 is shaped and dimensioned such that the block 725 is capable of being gripped by hand during a surgical procedure. For example, the block 725 may include a recess 730 on one or more ends, such as the end 725B as shown, to assist in gripping the block 725. However, in other embodiments the block 725 can have various shapes and dimensions.

As shown in FIG. 10B, the block 725 can have one or more guide attachment members 740. For the bone preparation instrument 720 as shown, the one or more guide attachment members 740 are included on the end 725A of the block 725. In one embodiment, the one or more guide attachment members 740 can be fixed to the block 725 on an end of the members 740 nearest the top end 725C and free on an end of the attachment members 740 nearest the bottom end 725D. In such a configuration, the one or more members 740 can extend out from the end fixed to the block 725 in a direction that is generally parallel to an axis of the block 725 extending from the top end 725C to the bottom end 725D. But in other configurations of the block 725 that include the guide attachment members 740, the members 740 can be fixed at various positions on the block 725 and extend out from the block 725 at any angle. In the embodiment shown, the members 740 assume a cylindrical shape.

The block 725 can additionally include a projection 750 that extends out from an end, such as the bottom end 725D as illustrated, of the block 725. In an exemplary application, the bottom end 725D of the block 725 can be positioned so as to interface with, for instance, two bones while the projection 750 is configured to extend into a space defined between the bones (e.g. a joint between two bones, or a space between two bone portions of a fractured bone). As such, depending on the application of the bone preparation instrument 720, the projection 750 may have a width 755 that is dimensioned so as to be able to fit into the space defined between bones as desired. As shown, the projection may assume the shape of a planar member having two surfaces separated by a distance. In the embodiment shown, the distance, 755, is generally constant, and a leading edge of the projection 750 is provided with a wedge to facilitate insertion into a space. In other embodiments, the distance may vary from a narrower dimension near the leading region to a wider dimension near a proximal region.

The bone preparation instrument 720 can also include one or more guide members 760 and/or 770 positionable with respect to the block 725. The guide members 760 and 770 may be made of an appropriate metal or any other suitable material. The guide members 760 and 770 can each have a flange 780 and a support 790. The flange 780 is connected to the support 790, and in some embodiments the flange 780 and the support 790 can be one integral component.

Each flange 780 may include a first guide surface 800A and a second guide surface 800B. The first and second guide surfaces 800A and 800B can be adjacent surfaces facing one another with a space defined in the flange 780 between the first and second guide surfaces 800A and 800B. The space is useful for receiving a cutting instrument, such as a saw blade, and the surfaces 800A and 800B are useful for holding the cutting instrument in a desired plane during a cutting operation. As shown, the first guide surface 800A can be a surface of the flange 780 immediately opposite a surface of the flange 780 that connects to the support 790, and the second guide surface 800B can be a surface of the flange 780 immediately opposite a surface of the flange 780 that can interface with the block 725. In the illustrated embodiment, the guide surfaces 800A and 800B are both single, continuous surfaces lacking any gap. In some embodiments (not illustrated), a guide surface, for instance the second guide surface 800B, can contain a gap such that the guide surface is not a single, continuous surface. The first guide surface 800A defines a first plane, while the second guide surface 800B defines a second plane. As shown, the first guide surface 800A and the second guide surface 800B can be configured such that the first plane is parallel to the second plane, with the space (defined in the flange 780) between. In further embodiments (not illustrated), the guide surfaces 800A and 800B can be configured such that the first and/or second planes are skewed. Although the guide surfaces 800A and 800B are shown to be on the flange 780, in other embodiments the guide members 760 and/or 770 may have the guide surfaces 800A and 800B (and thus the space defined between the guide surfaces 800A and 800B) at various locations. For example, the guide surfaces 800A and 800B could be included as part of the support 790, such that the space defined in the flange 780 between the guide surfaces 800A and 800B would instead be defined in the support 790.

The support 790 of each guide member 760 and 770 can include one or more fixation apertures 810A and/or 810B. The fixation apertures 810A and 810B extend through the support 790. Each of the fixation apertures 810A and 810B can receive, for example, a bone preparation fixation pin that extends through the support 790 at the fixation apertures 810A and 810B such that an end of the bone preparation fixation pin can be fixed to a bone. In the illustrated embodiment, the fixation apertures 810A and 810B are located on opposite ends of the support 790. Specifically, the fixation apertures 810A and 810B as shown are located on opposite ends of a longitudinal axis of the support 790 that extends perpendicular to the flange 780, and thus the first and second guide surfaces 810A and 810B. However, in other embodiments the support 790 can extend at various angles from the flange 780 and the one or more fixation apertures 810A and 810B can be positioned at various locations on the guide members 760 and 770 (e.g. the flange 780).

In some embodiments, the guide member 760 and/or 770 may be pivotally attached to the block 725 such that the guide member 760 and/or 770 can pivot with respect to the block 725. For example, in one embodiment, to pivotally attach the guide member 760 and/or 770 to the block 725 the guide member 760 and/or 770 may include an aperture 820 to receive the guide attachment member 740 of the block 725. The aperture may assume a cylindrical shape sized to mate with the attachment member 740. In the illustrated embodiment, the aperture 820 is included on an end of the flange 780 adjacent the first and second guide surfaces 800A and 800B, but in other variations the aperture 820 can be included at other locations on the guide member 760 and/or 770. Further, in some embodiments (not shown), the block 725 can include the aperture 820 and the guide member 760 and/or 770 can include the attachment member 740.

In either configuration, the aperture 820 can be aligned with the guide attachment member 740, and the guide member 760 and/or 770 can be attached to the block 725 by mating the attachment member 740 and the aperture 820. In some embodiments, the pivotable connection allows for the guide member 760 and/or 770 to slide along the attachment member 740 until the guide member 760 and/or 770 contacts a surface of the block 725. The guide member 760 and/or 770 can be free at an end opposite an end that contacts the block 725, which can allow the guide member 760 and/or 770 to translate along the guide attachment member 740 such that the guide members 760 and 770 may be at different elevations with respect to the block 725.

In the manner described, the guide member 760 and/or 770 is attached to the block 725 in a way that allows the guide member 760 and/or 770 to independently pivot with respect to the block 725 and to independently translate with respect to the block 725. The guide member 760 and/or 770 can be pivotally attached to the block 725 in numerous ways and at various locations on the block 725. For instance, as illustrated the guide members 760 and 770 are pivotally attached to the block 725 on the same end 725A of the block 725 and radially spaced from each other on that end 725A. In this configuration, the guide members 760 and 770 pivot about the block 725 at an end 725A opposite an end 725B of the block 725. Additionally, the embodiment shown has the guide members 760 and 770 configured to pivot with respect to the block 725 about parallel axes of rotation. However, in other variations the guide members 760 and 770 can be attached to the block 725 at numerous locations, such as on opposite ends 725A and 725B, and in various configurations.

Depending on the location of the connections, separate bone preparation instruments 720 may be provided for left-side and right-side anatomies (e.g., a preparation instrument for a left foot and a preparation instrument for a right foot). In the embodiment shown, the bone preparation instrument 720 is configured for a left foot. In some embodiments, a bone preparation instrument configured for a right foot would be a mirror image of the instrument 720 configured for a left foot.

FIG. 10C illustrates a perspective view of the bone preparation instrument 720. In the illustrated embodiment, the guide members 760 and 770 are pivotally attached to the block 725. A location where a bone is to be cut can vary depending on the particular surgical procedure being performed on the single surgical patient. In some applications, the guide member 760 and/or 770 can be aligned at the location to be cut by appropriately positioning the block 725 such that the space defined between the guide surfaces 800A and 800B of the guide member 760 and/or 770 is located at the location to be cut.

In some embodiments, it may be desirable to adjust the location of the guide member 760 and/or 770 relative to the block 725 so that the guide member 760 and/or 770 is aligned at the location desired to be cut. In the example shown in FIG. 10C, the guide member 760 has been pivoted about the block 725 so that the guide member 760 is appropriately aligned at the location to be cut. Specifically, the guide member 760 has been pivoted about the block 725 so that the space defined between the guide surfaces 800A and 800B is positioned at the location desired to be cut. Similarly, the guide member 770 has been aligned at a second location to be cut by pivoting the guide member 770 about the block 725 so that the space defined between the guide surfaces 800A and 800B is positioned at the second location desired to be cut. Depending on the particular application, the guide members 760 and 770 can be pivoted about the block 725 to differing degrees. Therefore, by pivotally attaching the guide member 760 and/or 770 to the block 725, bone cuts can be made at a wide range of locations. Further, because the projection 750 can be positioned within a joint, a longitudinal axis of the cut can be generally parallel with the projection while the plane of the cut can be angularly adjusted relative to the projection as desired.

As previously noted, the guide members 760 and 770 can be attached to the block 725 in a manner that allows the guide members 760 and 770 to translate with respect to the block 725, such as up and down along the respective guide attachment members 740. Configuring the guide members 760 and 770 to translate with respect to the block 725 allows the guide members 760 and 770 to be positioned at differing elevations, such as differing elevations along the guide members 740. This can be beneficial, for example, where the block 725 is positioned between two bones having differing elevations (i.e. differing heights). In such an application, the guide members 760 and 770 can translate with respect to the block 725 (e.g. along the respective guide attachment members 740) so that each guide member 760 and 770 rests on the respective bone on each side of the block 725, even though the bone on each side of the block 720 has a different elevation.

Additionally, configuring the guide members 760 and 770 to translate with respect to the block 725 can allow the block 725 to be removed, for instance from a space defined between bones, while the guide members 760 and 770 remain in place. In the embodiment of the bone preparation instrument 720 shown, the guide members 760 and 770 are free at an end opposite an end that can contact the block 725. This may allow the block 725 to be pulled away from the guide members 760 and 770 without disturbing the guide members 760 and 770, which may provide more working room during a surgical procedure.

During a surgical procedure the bone preparation instrument 720 can be positioned at a space defined between two bones. In particular, this can, for instance, include positioning the block 725 at the space defined between the bones. For embodiments where the block 725 includes the projection 750, the block 725 can be positioned at the space defined between the bones such that the projection 750 extends into the space defined between the bones. The projection 750 can, for example, assist in positioning and spacing the bones.

After positioning the bone preparation instrument 720, the guide members 760 and/or 770 can be aligned at the location(s) to be cut. Aligning the guide members 760 and 770 at the respective locations to be cut can include pivoting one or both guide members 760 and 770, for example at the apertures 820, about the block 725 as necessary. In addition, in some embodiments aligning the guide member 760 and/or 770 can include translating the guide member 760 and/or 770 relative to and along the block 725 such that an elevation of the guide member 760 and/or 770 can be adjusted, for instance, to match an elevation of the respective bones. The guide members 760 and 770 can be aligned such that cuts made to the bones using the respective guide members 760 and 770 are parallel cuts, but in other embodiments the guide members 760 and 770 can be aligned such that the cuts made to the bones are at various angles relative to each other.

Once the guide members 760 and/or 770 have been aligned at the respective locations to be cut, the guide members 760 and/or 770 can be fixed to the respective bones. In the illustrated embodiment, the bone preparation fixation pins (not shown) may be inserted through the fixation apertures 810A and/or 810B of the guide members 760 and/or 770 to fix the guide members 760 and/or 770 to the respective bones. An end of a bone preparation fixation pin can be inserted through, for example, the fixation aperture 810B in the support 790 such that the end of the bone preparation fixation pin is fixed to the respective bone.

After aligning and fixing the guide members 760 and/or 770, the block 725 may be removed from the space defined between the bones. The block 725 can be removed by pulling the block 725 away from the bones in a direction opposite the bones. As such, in embodiments where the block 725 includes the projection 750, the projection 750 can also be removed from the space defined between the bones by removing the block 725. In this manner, the block 725 can slide out from the guide members 760 and 770 while the guide members 760 and 770 remain fixed to the respective bones.

The bones can be cut at the desired locations where the guide members 760 and/or 770 have been aligned. For example, the cutting member (e.g. a saw blade) can be inserted through the space defined between the first and second guide surfaces 800A and 800B to cut the respective bone. The guide surfaces 800A and 800B can serve to direct the cutting member to the location of the bone to be cut, which in many applications of the bone preparation instrument 720 can be a precise location.

When the bones have been cut on the one surgical patient, the guide members 760 and/or 770 can be removed and the bone preparation instrument 720 can be discarded using conventional means. Removing the guide members 760 and/or 770 may include removing any bone preparation fixation pins from the bones as well as from the guide members 760 and/or 770. In some embodiments, the bones may then be compressed together and one or more bone plates may be applied.

Figure 11B:
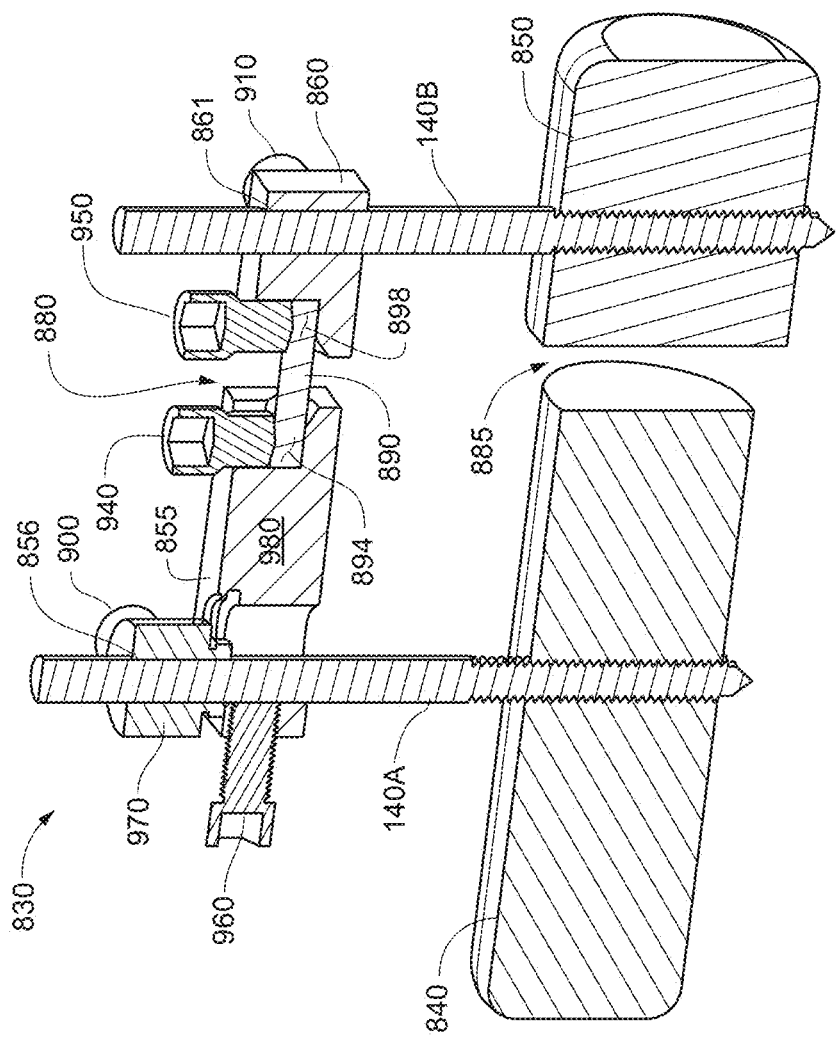

FIGS. 11A and 11B illustrate a third embodiment of a bone preparation instrument 830. The bone preparation instrument 830 can serve as a single bone preparation instrument included in embodiments the kit 10 and be disposed after use on a single surgical patient. FIG. 11A shows a perspective view of the bone preparation instrument 830, while FIG. 11B shows a perspective cross-sectional view of the bone preparation instrument 830. The bone preparation instrument 830 can be useful for temporarily fixing bones in a desired position during a surgical procedure, such as a bone alignment, osteotomy, and/or fusion procedure.

The bone preparation instrument 830 can include a first bone preparation fixation pin 140A for attachment to a first bone 840. A second bone preparation fixation pin 140B can be provided for attachment to a second bone 850, such as an adjacent bone separated by a joint or different portions of a single bone. As shown best in FIG. 11B, a first block 855 having a first aperture 856 can slidably receive the first bone preparation fixation pin 140A, and a second block 860 having a second aperture 861 can slidably receive the second fixation pin 140B. The first and second apertures 856, 861 can allow the first and second blocks 855, 860 to slide along a longitudinal axis of the first and second fixation pins 140A, 140B, respectively. The first and second apertures 856, 861 can also allow the first and second blocks 855, 860 to rotate about the longitudinal axis of the first and second fixation pins 140A, 140B, respectively. In some embodiments, the first and second fixation pins 140A, 140B are generally cylindrical and have a distal portion and a proximal portion, and the distal portion is threaded for retention within first and second bone, while the proximal portion is unthreaded for sliding within the first and second apertures and free rotational movement within the first and second apertures. In some embodiments, the proximal portion has a uniform diameter, such that it does not contain a flared or "head" portion. In such embodiments, the first and second blocks can be positioned on the first and second fixation pins before or after the pins are engaged with bone.

Again as best shown in FIG. 11B, a multi-axis joint 880 can be provided to connect the first block 855 and the second block 860 and located adjacent to a joint 885 between the first and second bones. In some embodiments, the multi-axis joint 880 allows the first block 855 and the second block 860 to move with respect to each other about more than one axis. In certain embodiments, the multi-axis joint 880 allows the first block 855 and the second block 860 to move with respect to each other about the three cardinal planes (i.e., X, Y, and Z axes). In the embodiment shown, the multi-axis joint 880 allows for angulation in all directions and rotation between the first and second blocks. In other examples, the bone positioning instrument 830 can be attached to first and second bones 840, 850, where the first and second bones are skewed relative to each other. In this case, a longitudinal axis of second bone 850 is skewed, for example, about 15 degrees relative to a longitudinal axis of first bone 840.

The multi-axis joint can include any suitable structure for allowing desired adjustments about more than one axis. In some embodiments, with reference to FIG. 11B, the multi-axis joint 880 includes a link 890 having a first end 894 rotatably connected to the first block 855 and a second end 898 rotatably connected to the second block 860. Such a multi-axis joint allows for the movement about the various axes discussed above at both the first end and the second end. In the embodiment shown, the first end 894 includes a first ball received within a first socket of the first block 855, and the second end 898 includes a second ball received within a second socket of the second block 860.

Some embodiments of the instrument 830 allow the relative positions of the first and second bones to be fixed after a desired orientation has been achieved. For example, a first set screw 900 can extend through the first block 855 into the first aperture 856 and be positioned against the first fixation pin 140A, for fixation of the first block on a longitudinal axis of the first fixation pin and/or about the longitudinal axis of the first fixation pin. Further, a second set screw 910 can extend through the second block 860 into the second aperture 861 and be positioned against the second fixation pin 140B, for fixation of the second block on a longitudinal axis of the second fixation pin and/or about the longitudinal axis of the second fixation pin. In certain embodiments, the first and second set screws are positioned perpendicular to the first and second fixation pins. As shown in FIG. 11A, additional set screws 920, 930 extending through the first and second blocks can be positioned opposite of the first and second set screws, respectively. Such oppositely positioned set screws facilitate the use of the bone positioning device to be utilized, for example, on a left foot or a right foot.

Set screws can also be provided to fix positions across the multi-axis joint. In the embodiment shown in FIG. 11B, a first end set screw 940 extends through the first block 855 and is positioned against the first end 894 of the link 890. Further, a second end set screw 950 is shown extending through the second block 860 and positioned against the second end 898 of the link 890.

In some surgical procedures on a single surgical patient, the instrument 830 can be used to apply a compression force between two adjacent bones, or different portions of a single bone, while the bones are held in desired alignment and/or to facilitate a desired alignment between the bones. Such a compression force is useful for a surgical procedure such as bone fusion, for example. As shown in FIG. 11B, in some embodiments the instrument 830 includes a compression screw 960 operable to exert a compression force between first and second bones 840, 850 connected to first and second fixation pins 140A, 140B, respectively. In the embodiment shown, the compression screw 960 is generally perpendicular to the fixation pins and is threadingly received within a block and positioned to act against one of the fixation pins.

One of the blocks can be adapted to allow for relative movement to exert the compression force. In the embodiment shown in FIG. 11B, one of the blocks (e.g., the first block 855) has a first portion 970 slidingly connected to second portion 980. An aperture (e.g., the first aperture 856) extends through the first portion and the second portion. In this embodiment, the first aperture has a first cross-sectional area in the first portion and a second cross-sectional area in the second portion, and the first cross-sectional area is smaller than the second cross-sectional area. The set screw 900 can extend through the first portion 970. The compression screw 960 can extend through the second portion 980. Upon actuation, the compression screw 960 will act against the fixation pin 140A and will pull the second portion 980 of the block 855 away from the fixation pin 140A. The force will be transmitted through the multi-axis joint 880 through the other block 860 and fixation pin 140B, thereby applying a compression force that tends to press together leading surfaces of the first and second bones 840, 850.

As will be appreciated, the bone preparation instrument 830 can find particular use in positioning one or more bones on the single surgical patient. Once the one or more bones no longer need to be positioned using the instrument 830, the instrument 830 can be discarded using conventional means.

Depending on the particular surgical procedure for which a specific embodiment of the kit 10 is intended, one of the three bone preparation instruments 520, 720, or 830 can be included in the kit 10, and no other bone preparation instrument need be included.

Figure 12:
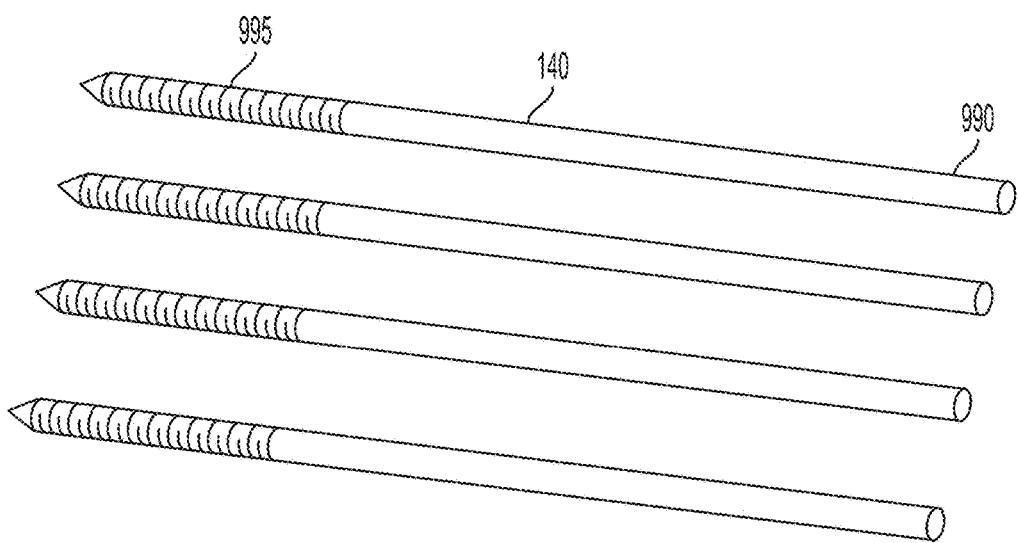
FIG. 12 is a perspective view of one embodiment of bone preparation fixation pins.

FIG. 12 illustrates a perspective view of bone preparation fixation pins 140, shown and described as included in the kit 10 with respect to FIG. 1. The bone preparation fixation pins 140 can be used in conjunction with any one of the bone preparation instruments 520, 720, or 830 to fixate the bone preparation instrument to one or more bones and provisionally position bones with respect to each other (e.g., rotationally, translationally, and/or elevationally) after removal of the bone preparation instrument and prior to installation of a bone plate. The bone preparation fixation pins 140 can include a first end 990 and a second end 995. The second end 995 can be pointed and optionally threaded or fluted and inserted through an aperture of a bone preparation instrument and into a bone. Because the bone preparation fixation pins 140 can be used across the various embodiments of the bone preparation instruments, efficiency is achieved when packing multiple kits 10 that each include a different single bone preparation instrument. Once the surgical procedure on the one surgical patient is finished, the at least one and no more than ten (e.g., 2, 4, 6, or 8) bone preparation fixation pins 140 included in a kit 10 can be discarded using conventional means.

Although not shown, some embodiments of the kit 10 can include at least one and no more than two cutting instruments. For example, an embodiment of the kit 10 can include at least one and no more than two saw blades. The saw blades can be used to cut one or more bones, such as in conjunction with a bone preparation instrument. Once the bone or bones are cut as desired for the specific surgical procedure on the single surgical patient, the at least one and no more than two saw blades can be discarded.

Some embodiments of the kit 10 may also include at least one and no more than four reamer sets (e.g., each having 1, 2, 3, or 4 reamers). The reamer can be used to prepare a surface of one or more bones and/or drill a hole in one or more bones. After appropriate surface preparation and/or hole creation has been completed as needed for the particular surgical procedure on the single surgical patient, the at least one and no more than four reamer sets can be discarded. Further examples of the kit 10 that include at least one and no more than four reamer sets may also include a single reamer sizing template. In one instance, the single reamer sizing template can be integral to the container 20 such that when a reamer is to be removed from the kit 10 during a surgical procedure the reamer can be placed on the reamer sizing template to determine a dimension (e.g. length, diameter) of the chosen reamer. In other instances, the reamer sizing template can be a separate component included in the kit 10 that is removable from the container 20 so as to allow a dimension of the reamer to be determined external to the container 20. Once the specific surgical procedure has been completed on the single surgical patient, the reamer sizing template can be discarded.

Although not shown, some embodiments of the kit can include one or more implants. For example, one or more implants useful for filling a bone void created during a surgical procedure, such as, for example, a metatarsal base wedge procedure or an Evens lengthening procedure, may be provided. Examples of such a one or more implant include an allograft bone wedge, a titanium bone wedge, a titanium wedge, a synthetic bone wedge, or any other bone substitute.

In sum, various embodiments of the disposable single-use kit 10 can include all or any combination of one or more of the described surgical items. The items to be included in the kit 10 will vary depending on the specific surgical procedure for which the kit 10 is intended to be used. Items included in the kit 10 can be within the quantity ranges described herein, and the kit, including all of the surgical items included in the kit 10, may be discarded after use on a single surgical patient. Some embodiments of the kit can include all components in a single sterile package. Other embodiments of the kit can include two or more sterile packages with different components in each sterile package. For example, a first sterile package containing the bone plates, fasteners, and pins may be provided along with a second sterile package containing instruments such as plate manipulation and/or bone preparation instruments. Such a kit can also be provided in modular form with components grouped together in separate sterile packages to be selected to provide a complete kit for the desired surgical procedure.

Thus, embodiments of the invention are disclosed. Although the present invention has been described with reference to certain disclosed embodiments, the disclosed embodiments are presented for purposes of illustration, and not limitation, and other embodiments of the invention are possible. One skilled in the art will appreciate that various changes, adaptations, and modifications may be made without departing from the spirit of the invention.

The invention claimed is:

1. A disposable single-use surgical kit for a foot or ankle orthopedic procedure comprising:
   a sterile container;
   a plurality of unicortical bone plate fasteners included in the sterile container; and
   at least one bone plate but no more than four bone plates included in the sterile container, each bone plate comprising:
      a body having a top surface and a bone facing surface opposite the top surface; and
      a first fixation hole extending through the body from the top surface to the bone facing surface and configured for receiving one of the plurality of unicortical bone plate fasteners included in the sterile container,
   wherein at least one bone plate of the at least one but no more than four bone plates comprises the body extending from a proximal region to a distal region and having a helical curvature between the proximal region and the distal region.

2. The kit of claim 1, wherein each bone plate is configured to be positioned across a tarsal-metatarsal joint for tarsal-metatarsal joint fusion.

3. The kit of claim 1, wherein the at least one bone plate but no more than four bone plates is two bone plates, a first one of the two bone plates being configured to span from a dorsal region of a medial cuneiform to a medial region of a first metatarsal and a second one of the two bone plates being configured to span from a plantar region of the first metatarsal to a medial region of the medial cuneiform.

4. The kit of claim 3, wherein each of the two bone plates has four fixation holes with two of the four fixation holes positioned on a distal region of the bone plate and two of the four fixation holes positioned on a proximal region of the bone plate.

5. The kit of claim 4, wherein the plurality of unicortical bone plate fasteners is at least eight.

6. The kit of claim 1, wherein the helical curvature comprises both a bend of the body along a central longitudinal axis and a twist of the body about the central longitudinal axis, and wherein the distal region lies in a first plane and the proximal region lies in a second plane offset from the first plane both along and about the central longitudinal axis such that the helical curvature provides a transition from the first plane to the second plane.

7. The kit of claim 1, wherein each of the plurality of unicortical bone plate fasteners is sized to be inserted through a fixation hole of a bone plate and through one cortical wall of at least one of a first metatarsal and a medial cuneiform but not an opposed cortical wall of the at least one of the first metatarsal and the medial cuneiform.

8. The kit of claim 1, wherein a number of the plurality of unicortical bone plate fasteners included in the sterile container is greater than or equal to a total number of fixation holes of the bone plates included in the sterile container.

9. The kit of claim 1, wherein a number of the plurality of unicortical bone plate fasteners included in the sterile container is equal to a total number of fixation holes of the bone plates included in the sterile container plus at least one and no more than four, and no other bone plate fasteners are included in the sterile container.

10. The kit of claim 1, wherein the bone facing surface of each bone plate includes a pad extending out a distance from a first surface.

11. The kit of claim 10, wherein the pad extends out the distance from the first surface at a location on the bone facing surface adjacent the first fixation hole.

12. The kit of claim 1, wherein the body has a length defining a central longitudinal axis and a width defining an extent of the bone plate transverse to the central longitudinal axis, and wherein the width of the body is greater at a location along the central longitudinal axis having the first fixation hole compared to the width of the body at a location remote from the first fixation hole.

13. The kit of claim 1, wherein at least one bone plate further comprises one of the plurality of unicortical bone plate fasteners at least partially within the first fixation hole.

14. The kit of claim 1, wherein each one of the plurality of unicortical bone plate fasteners included in the sterile container comprises a head and a shaft, wherein the shaft of each one of the plurality of unicortical bone plate fasteners consists of one of one of two lengths, and there are no other lengths of bone plate fasteners within the sterile container.

15. The kit of claim 1, wherein each one of the plurality of unicortical bone plate fasteners included in the sterile container comprises a head and a shaft, wherein the shaft of each one of the plurality of unicortical bone plate fasteners consists of one of a first diameter, a second diameter, a third diameter, and a fourth diameter, and there are no other diameters of bone plate fasteners within the sterile container.

16. The kit of claim 1, further comprising at least one and no more than three plate manipulation instruments included in the sterile container.

17. The kit of claim 16, wherein at least one of the plate manipulation instruments includes an end configured to drive one of the plurality of unicortical bone plate fasteners received within the first fixation hole into a bone.

18. The kit of claim 1, further comprising a bone preparation instrument included in the sterile container.

19. The kit of claim 18, further comprising at least one and no more than ten bone preparation fixation pins included in the sterile container.

20. The kit of claim 1, further comprising at least one and no more than six bone cut pins included in the sterile container.

21. The kit of claim 20, wherein at least one of the bone cut pins includes a collar at a location on the bone cut pin spaced from an end of the bone cut pin.

22. The kit of claim 1, further comprising at least one and no more than four bone fixation pins included in the sterile container.

23. The kit of claim 22, wherein each of the bone fixation pins includes a collar at a location on the bone fixation pin spaced from an end of the bone fixation pin.

24. The kit of claim 1, further comprising at least one and no more than three external fasteners included in the sterile container and at least one and no more than three washers sized to receive the at least one and no more than three external fasteners.

25. The kit of claim 1, further comprising at least one and no more than two external fasteners included in the sterile container, wherein the at least one and no more than two external fasteners have a length different than a length of each one of the plurality of unicortical bone plate fasteners included in the sterile container, and further including at least one and no more than two washers sized to receive the at least one and no more than two external fasteners.

26. The kit of claim 1, further comprising at least one and no more than two saw blades included in the sterile container.

27. The kit of claim 1, further comprising at least one and no more than four reamer sizes.

28. A method for performing a surgical operation, the method comprising the steps of:
removing a plurality of bone plate fasteners from a sterile container, wherein each one of the plurality of bone plate fasteners comprises a head and a shaft, and wherein the shaft of each one of the plurality of bone plate fasteners consists of one of a first length, a second length, a third length, and a fourth length, and further wherein the diameter of each one of the plurality of bone plate fasteners consists of one of a first diameter, a second diameter, a third diameter, or a fourth diameter, and there are no other lengths or diameters of bone plate fasteners within the sterile container;
removing at least one and no more than four bone plates from the sterile container, the at least one and no more than four bone plates each comprising:
a body having a top surface and a bone facing surface opposite the top surface; and
a first fixation hole extending through the body from the top surface to the bone facing surface and configured for receiving one of the plurality of bone plate fasteners;
contacting a bone with the at least one and no more than four bone plates removed from the sterile container; and
inserting one of the plurality of bone plate fasteners removed from the sterile container through the first fixation hole and into the bone,
wherein removing at least one and no more than four bone plates comprises removing a bone plate comprising the body extending from a proximal region to a distal region and having a helical curvature between the proximal region and the distal region.

29. The method of claim 28, wherein contacting the bone with the at least one and no more than four bone plates removed from the sterile container comprises contacting the bone with a pad extending out a distance from the first surface of each of the at least one and no more than four bone plates.

30. The method of claim 28,
wherein removing at least one and no more than four bone plates from the sterile container is removing two bone plates from the sterile container, and
contacting the bone comprises positioning each of the two bone plates across a tarsal-metatarsal joint.

31. The method of claim 30, wherein the plurality of bone plate fasteners comprise unicortical bone plate fasteners, and inserting one of the plurality of bone plate fasteners comprises inserting one of the plurality of unicortical bone plate fasteners.

32. The method of claim 28, further comprising:
removing at least one and no more than ten bone preparation fixation pins from the sterile container; and
fixing the single bone preparation instrument to the bone at a position near the bone location to be cut using the at least one and no more than ten bone preparation fixation pins.

33. The method of claim 28, further comprising:
removing at least one and no more than three plate manipulation instruments from the sterile kit;
inserting an end of one of the plate manipulation instruments into an attachment member configured at least partially within the first fixation hole of one of the bone plates removed from the sterile container; and
bending one of the bone plates while the end of the plate manipulation instrument is inserted in the attachment member.

* * * * *